(12) United States Patent
Ito et al.

(10) Patent No.: US 7,766,890 B2
(45) Date of Patent: Aug. 3, 2010

(54) PAPER DIAPER

(75) Inventors: Kazunori Ito, Iyomishima (JP); Hiroshi Ono, Iyomishima (JP); Tomoka Kamoto, Iyomishima (JP)

(73) Assignees: Daio Paper Corporation, Ehime (JP); Daio Paper Converting Co., Ltd., Ehime (JP)

( * ) Notice: Subject to any disclaimer, the term of this patent is extended or adjusted under 35 U.S.C. 154(b) by 423 days.

(21) Appl. No.: 10/469,791

(22) PCT Filed: Mar. 1, 2002

(86) PCT No.: PCT/JP02/01905

§ 371 (c)(1),
(2), (4) Date: Mar. 31, 2004

(87) PCT Pub. No.: WO02/069873

PCT Pub. Date: Sep. 12, 2002

(65) Prior Publication Data

US 2004/0153046 A1 Aug. 5, 2004

(30) Foreign Application Priority Data

Mar. 3, 2001 (JP) ............................. 2001-109227
Mar. 3, 2001 (JP) ............................. 2001-109228

(51) Int. Cl.
*A61F 13/15* (2006.01)
*A61F 13/20* (2006.01)
(52) U.S. Cl. ...................................... 604/391; 604/386
(58) Field of Classification Search .................. 604/390, 604/391, 386; 24/445, 448, 442
See application file for complete search history.

(56) References Cited

U.S. PATENT DOCUMENTS 1,908,328 A * 5/1933 Dreyfus .................. 139/426 R
4,704,238 A 11/1987 Okuyama et al.

(Continued)

FOREIGN PATENT DOCUMENTS

AU 764673 B2 * 8/2000

(Continued)

OTHER PUBLICATIONS

Complete Textile Glossary (excerpts only), Celanese Acetate, 2001.*

(Continued)

*Primary Examiner*—Melanie J Hand
(74) *Attorney, Agent, or Firm*—Frishauf, Holtz, Goodman & Chick, P.C.

(57) ABSTRACT

A disposable diaper includes a hook and loop fastener which includes: (i) a plurality of hook components, which are fixed in place on both lateral sides of a rear side of the disposable diaper, and (ii) a hook receiving component that is fixed in place at a belly side of the disposable diaper. The hook components are engageable with the hook receiving component to form a fixing member for putting the disposable diaper on a user. The hook receiving component includes a base material section having a target that is visible from a front surface side of the hook receiving component, and a plurality of loops which are fixed in place on a surface of the base material section. Each of the loops is formed of a non-crimp treated continuous filament yarn that is straight or slowly curved.

3 Claims, 19 Drawing Sheets

U.S. PATENT DOCUMENTS

| | | | |
|---|---|---|---|
| 4,739,635 A | | 4/1988 | Conley et al. |
| 4,902,553 A | * | 2/1990 | Hwang et al. ............... 428/156 |
| 4,973,326 A | * | 11/1990 | Wood et al. ................. 604/391 |
| 5,392,498 A | * | 2/1995 | Goulait et al. ................. 24/452 |
| 5,403,302 A | * | 4/1995 | Roessler et al. ............. 604/391 |
| 5,473,800 A | * | 12/1995 | Hatomoto et al. ............. 24/442 |
| 5,683,634 A | | 11/1997 | Fujii et al. |
| 5,759,678 A | * | 6/1998 | Fujii et al. ............... 428/315.5 |
| 5,761,775 A | | 6/1998 | Legome et al. |
| 5,851,205 A | * | 12/1998 | Hisada et al. ............... 604/390 |
| 5,858,515 A | * | 1/1999 | Stokes et al. ............. 428/195.1 |
| 5,875,526 A | | 3/1999 | Yamaguchi |
| 5,897,546 A | | 4/1999 | Kido et al. |
| 5,962,102 A | * | 10/1999 | Sheffield et al. ............... 428/92 |
| 6,632,974 B1 | * | 10/2003 | Suzuki et al. ................. 604/369 |
| 6,653,249 B1 | * | 11/2003 | Blumenthal ................. 442/59 |
| 6,770,065 B1 | * | 8/2004 | Sasaki et al. ................. 604/391 |
| 2002/0028624 A1 | * | 3/2002 | Mizutani et al. ............ 442/394 |

FOREIGN PATENT DOCUMENTS

| | | | |
|---|---|---|---|
| JP | 01-168901 A | | 7/1989 |
| JP | 01-244845 A | | 9/1989 |
| JP | 02-127445 A | | 5/1990 |
| JP | 05-076569 A | | 3/1993 |
| JP | 09-038138 A | | 2/1997 |
| JP | 09-308510 A | | 12/1997 |
| JP | 10-085012 A | | 4/1998 |
| JP | 10102345 A | * | 4/1998 |
| JP | 10-309299 A | | 11/1998 |
| JP | 11-042252 A | | 2/1999 |
| JP | 2000-000266 A | | 1/2000 |
| JP | 2000-070010 A | | 3/2000 |
| JP | 2000-157569 A | | 6/2000 |
| JP | 2001-054536 A | | 2/2001 |
| KR | 0158551 B1 | | 12/1998 |
| KR | 1999-0014162 A | | 2/1999 |
| KR | 10-0235124 B1 | | 12/1999 |
| WO | WO 99/60881 A1 | | 12/1999 |
| WO | WO 00/42964 A1 | | 7/2000 |

OTHER PUBLICATIONS

Japanese Office Action (and English translation thereof) dated Jun. 20, 2008, issued in counterpart Japanese Patent Application No. 2001-109227.

Japanese Office Action (and English translation thereof) dated Jun. 20, 2008, issued in counterpart Japanese Patent Application No. 2001-109228.

A Korean Office Action (and English translation thereof) dated Oct. 13, 2008, issued in counterpart Korean Application No. 2008-7022150.

A Japanese Office Action (and English translation thereof) dated Sep. 26, 2008, issued in counterpart Japanese Application No. 2001-109227.

A Japanese Office Action (and English translation thereof) dated Sep. 26, 2008); issued in counterpart Japanese Application No. 2001-109228.

Korean Office Action dated Dec. 11, 2008, and English translation thereof issued in a counterpart Korean Application No. 10-2003-7011545.

Korean Office Action dated Nov. 20, 2009 and English translation thereof issued in a counterpart Korean Application No. 10-2003-7011545.

* cited by examiner

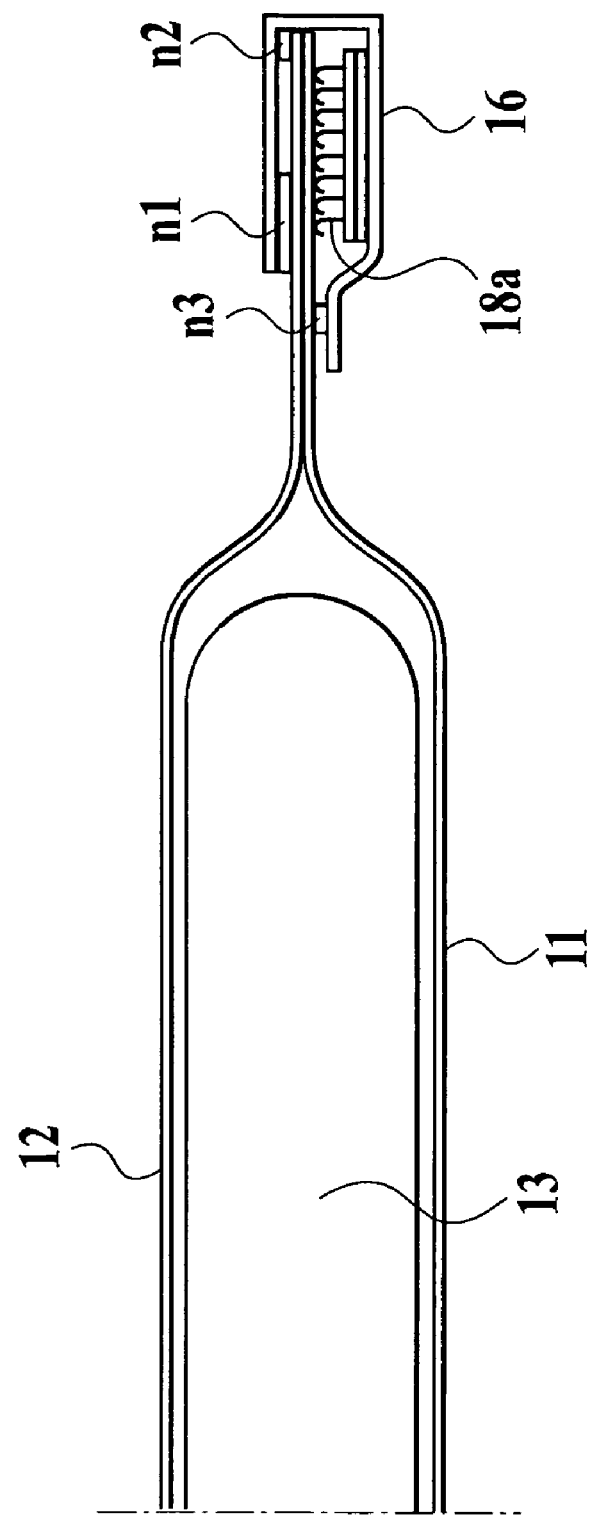

PAPER DIAPER

This application is a U.S. National Phase Application under 35 U.S.C. 371 of International Application PCT/JP02/01905, filed Mar. 1, 2002.

FIELD OF THE INVENTION

The present invention relates to a disposable diaper. More particularly, the present invention relates to the fastening of the disposable diaper.

BACKGROUND ART

Generally, as a tape fastener when the disposable diaper is put onto a wearer, the one which utilizes an adhesive is mainly used. In a diaper cover, bonding is made by using a detachable hook and loop fastener which engages a hook component with an hook receiving component (generally, called VELCRO Fastener (registered trademark) or MAGIC Tape (registered trademark)). When this hook and loop fastener is used, it is detachable many times and is convenient.

On the contrary, the disposable diaper with a structure where an adhesive tape fastener is fixed in place at both side portions of the disposable diaper, the larger area of the front sheet is fixed in place on the back sheet surface of the belly side of the disposable diaper, the adhesive tape fastener is fastened to this front sheet and the mounting position can be adjusted, is widely and generally used.

In this case, the one where the targets (marking) are formed by printing on the front tape with spaced relationship each other in a belly peripheral direction is known for convenience sake's of the fastening position of the adhesive tape fastener.

For the one with a structure where the adhesive tape fastener is intended to be fastened to the front sheet, although there is an advantage that the mounting position of the tape fastener can be adjusted, when the fastener is once taken off after wearing to confirm whether or not there is a urination and is fastened again to the front sheet, the fastening strength of the adhesive deteriorates. Further, since it primarily relies upon the adhesion strength by the adhesive, for example, in the adult disposable diaper having a larger area, it results in insufficient strength, thereby peeling off is likely to take place.

In this regard, when the hook and loop fastener is used, there is an advantage that a larger engagement strength can be obtained, and although detachable actions are repeated, the engagement strength does not deteriorate. As the hook and loop fastener in this case, the one where the hook component comprises a number of inverted L-shape-like or mushroom-like protrusions, the hook receiving component comprises a number of almost half-arced loops whose both ends are fixed at the surface of the base material section, thus both elements are mechanically detachable (peeling off) by the entanglement of both elements in place of an adhesion power or a chemical bond is generally used. In addition, a filament yarn (a single filament is illustrated in f) on which crimp treatment (bulky treatment) is performed as loops $5a, 5a, \ldots$ is conventionally used as enlarged and shown in FIG. 11, the bulkiness allows the filament yarn to realize a firm entanglement with the hook component. In addition, even if a hook and loop fastener is used in place of a front tape likewise, the one where the targets which are formed in the base material section $5b$ is marketed.

However, in the conventional hook receiving component of the conventional hook and loop fastener, there was a problem that the targets (not illustrated) on the surface of the base material section $5b$ were dispersedly hidden by a number of loops $5a, 5a, \ldots$ on the surface of the base material section as shown in FIG. 11 mainly by "the bulkiness of the fiber comprising the loops", although a character or a designed pattern was arranged as a target, the target could not be clearly observed.

Therefore, the subject of the present invention is intended to allow the target on the base material section in the hook receiving component to be clearly observed in the hook and loop fastener which functions as the fastening member of the disposable diaper.

Another subject is intended to provide an air permeable product even in the fastening front sheet portion.

In addition, the tape-type disposable diaper conventionally marketed is as follows. This is one where a fastening piece in which an adhesive layer is formed on the fastened surface is provided on both sides of the back side of the disposable diaper for wearing, when it is used, after the corresponding portions of the wearer's body are each covered with the front side and back side of the disposable diaper, the fastening piece is brought into the belly side, and the disposable diaper is fixed in place by fastening the fastening piece onto the front target tape comprising the plastic materials such as polyethylene fixed in place by the adhesive on the surface of non-liquid permeable sheets such as polyethylene sheets on the external surface of the disposable diaper.

In the relevant tape-type disposable diaper, it is difficult to tightly fasten the disposable diaper by fastening only once, the adjustment of fastening of the disposable diaper may be actually repeated several times until it is tightly fastened in place. As one of the causes of the adjustment of fastening, a case that although one piece of a pair of fastening pieces could be fastened onto the front target tape, the other fastening piece could not reach the front target tape can be taken up. In fastening, a user felt troublesome in a case per se that the fastening position of the fastening piece was limited.

In addition, there was a case that the front target tape was torn while fastening was adjusted several times. Of course, although tearing of the front target tape can be prevented by increasing the thickness of the target tape. However, when the rigidity of the front target tape is increased, the disposable diaper becomes bulky and the comfortable wearing property may be lost. Thus, the present status is that it copes with situation by minimizing the thickness.

In order overcome these problems, the applicants have previously proposed the disposable diaper in Japanese Patent Application No. 11-273799 where the entire external sheet was formed of non-woven cloth and a mechanical fastening pieces are detachably engaged at an arbitrary position on the surface of the belly. This disposable diaper brings about the advantages that a disposable diaper dispenses with the front target tape made of polyethylene or the like attached to the surface of the belly so as to eliminate troublesomeness when the fastening piece is fastened and improve the wearing property, and improvement of the productivity, reduction of the production cost or the like can be accomplished by removing the front target tape.

However, the relevant disposable diaper with no front target tape is such that although there is no troublesomeness in wearing the disposable diaper since the fastening position of the fastening piece is not limited, a user, in turn, has a difficulty using the disposable diaper when the index of the fastening position is not provided.

Another subject according to the present invention is intended to facilitate tape fastening work while eliminating troublesomeness in fastening the fastening piece, improving comfortable feeling, increasing productivity and reducing cost by dispensing with the front target tape.

DISCLOSURE OF THE INVENTION

The inventors herein have thoroughly studied and found that there are mainly "the thick bulky height of a fiber comprising the loop", "the density of the number of the loops (number of loops per unit area)" and "the ordinality of loop disposition" as the factors which affect the easiness of looking the target on the base material portion in the hook receiving component having the loops. The findings are sequentially described.

In the first place, it is considered that "the thick bulky height of a fiber comprising the loop" mostly affect the easiness of looking the target. When the fiber comprising the loops is the crimp-treated filament yarn as in a conventionally used one (see the enlarged portion of FIG. 11), the masked area is excessive and the lower target can be hardly observed. Although the thickness of the loop can not be primarily determined since it is a filament yarn, in a conventional crimp-treated article, the thickness of almost all loops are 400 µm or more.

Next, for "density of the number of loops", when it mostly exceeds 60 pcs/cm$^2$, particularly, when it exceeds 50 pcs/cm$^2$, the masking action becomes conspicuous in case of visually observing the loops. In addition, when the loops are too scarce, the loops only become conspicuous, the lower target tends to be hardly observed. Therefore, the density of the number is determined to be 10 pcs/cm$^2$, preferably 30 pcs/cm$^2$ and more preferably 40 pcs/cm$^2$ or more.

Further, "the ordinality of loop disposition" is also important. When many of loops 5a, 5a, . . . are randomly disposed as shown in FIG. 11, they tend to be more hardly observed than in an actual masking ratio. However, when loops 5a, 5a, . . . are regularly disposed as shown in FIG. 10, it is easy to assume the masked portions, and a user feels easier to see them than in an actual masking ratio. Concretely, it is found that when 60 to 70% or more of many loops, particularly, 80 to 90% or more is observed in a form as if they were swollen and protruded toward a predetermined same direction as the base material section is viewed from the top, a user feels easier to see them than in the actual masking ratio.

In addition, "the length of a loop" is related to "the ordinality of loop disposition", when the length of one loop exceeds 3 mm, particularly 2 mm, the masking action by itself is conspicuous when visually inspected. In addition, when the loop becomes longer, the masking area by itself becomes larger and the binding power generated by fixing to the base material section does not act on the entire loop. Thus, the fibers are unbound and the loop becomes thicker as mentioned above, or the loop is irregularly distorted by its twisting or the like because the free portion becomes longer. Accordingly, the loops are irregularly disposed as a whole and it may be more hardly observed than in the actual masking ratio.

On the other hand, as the front sheet in the actual disposable diaper, the hook receiving component comprising the base material section 5b or 15b on which the target is arranged, a number of loops 5a, 5a, . . . or 15a, 15a, . . . which are fixed on the surface of this base material section 5b or 15b, and a grid net-like body 20 or 120 where a number of the loops 5a, 5a, . . . or 15a, 15a, . . . are assembled so as to allow a number of the loops 5a, 5a, . . . or 15a, 15a, . . . to be swollen and protruded is used. Thus, in the form of supplementing the adhesion of the loops 5a, 5a, . . . or 15a, 15a, . . . to the base material sections 5b or 15b by the grid net-like portions, "thick bulky height of the longitudinal fiber portion 5c or 15c and lateral fiber portion 5d or 15d" or "the longitudinal fiber potion spacing and lateral fiber portion spacing" in the grid net-like material also affect the easiness of looking the target of the base material section 5b or 15b. The affection of the latter is the same as in the density of the number of loops.

As we examine the matter like this, although it is found that all of the aforementioned factors synergistically act, the affection of the thick bulky height and the density of the number of the loop are great among them. However, when the thick bulky height of the loop in a conventional hook receiving component is merely reduced or the density of the number is merely reduced, the engagement power with the hook component deteriorates, and there is a possibility where the basic fastening function is lost. Although this problem can be solved by increasing the density of the number of the loops, when the density of the number is excessively increased, the problem that the easiness of looking the target on the base material section is damaged cannot be, in turn, solved.

The present invention has been done based on these findings and adopts the following constitutions.

According to the first aspect in the present invention, a disposable diaper comprises a hook and loop fastener which has a combination of a hook component and a hook receiving component, which are detachably engaged and which is used as a fixing member at a time of putting the disposable diaper on a user, the hook component of the hook and loop fastener being fixed in place at both sides on a rear side of the disposable diaper, and the hook receiving component being fixed in place at the belly side, wherein the hook receiving component comprises a base material section having a visible target from a front surface side and a number of loops fixed in place on a surface of the base material section, each of the loops being formed of continuous a filament yarn.

According to the disposable diaper having a fastening front sheet thus structured, a masking area is considerably made small even if the same number of filament yarns are used by utilizing a crimp-treated or preferably, a non-crimp treated straight or slowly curved filament yarns, and the target is easily observed. Namely, this allows the target to be easily observed without changing the size and number of filament yarns and lowering the strength, accordingly.

In the disposable diaper having the fastening front sheet like this, preferably, the density of the number of the loops may be 10 to 60 pcs/cm$^2$.

By setting the scope of the density of the number of the relevant loops, a sufficient fastening power can be exerted even if the crimp-treated or preferably, non-crimp treated straight or slowly curved filament yarns are used. In addition, when the density of the number of the loops stays within this range, although it is considered that the masking effect becomes larger by a thick disposition at a glance, when it is visually inspected in reality, the lower target can be even more easily observed than that of a conventional product where the loops are thinly disposed since the feelings of the material closer to those of the base material section itself can be conceived.

According to the second aspect in the present invention, a disposable diaper comprises a hook and loop fastener which has a combination of a hook component and a hook receiving component, which are detachably engaged and which is used as a fixing member at a time of putting the disposable diaper on a user, the hook component of the hook and loop fastener being fixed in place at both sides on a rear side of the disposable diaper, and the hook receiving component being fixed in place at the belly side, wherein the hook receiving component comprises a base material section having a visible target from a front surface side, and a grid-like or net-like body comprising a grid-like or net-like filament yarn member and loops of filament yarn, which are fixed in place on a surface of the base material section.

The present invention relates to an example where the adhesion of the loop to the base material section is supplemented by a grid-like or a net-like portion, in this regard, the target of the lower base material section can be easily observed by changing all the fibers existing on the base material section to a crimp-treated or preferably, a non-crimp treated straight or slowly curved filament yarns.

In addition, in the disposable diaper having the fastening front sheet like this, a constitution may be also so made that the density of the number of the loops is 10 to 60 pcs/cm$^2$, the longitudinal fiber portion spacing in the grid-like net body is 1.5 mm or less and the lateral fiber portion spacing is 3.0 mm or less.

Thus, the lower target can be further more easily observed as in the first aspect according to the present invention by setting the density of the number of the loops to 10 to 60 pcs/cm$^2$, setting the longitudinal fiber portion spacing to 1.5 mm or less and setting the lateral fiber spacing to 3.0 mm or less, that is, by more densely forming the loops or the grid than those of a conventional product, and an advantage that the adhesion strength to the base material section is increased is also brought about.

In addition, in the present invention, when the hook receiving component is observed from the top, a form may be also made that the loops of 60% or more are observed to be swollen and protruded in a predetermined direction.

The loops are more easily observed in than in the actual masking ratio as mentioned above by regularly disposing the loops like this.

It is preferred that the single hook receiving component has a light transmittance of 60% or less.

The target of the base material section can be more easily observed by suitably combining the aforementioned constitution according to the present invention to set the light transmittance to the aforementioned range.

The loops may be also fixed on the base material section with a polyurethane series adhesive.

The use of the relative adhesive can suppress the luster on the surface of the base material section, thereby the target of the base material section can be more easily observed.

The target may have a design which shows a plurality of different fastening positions in a body peripheral direction.

The arrangement of the relevant design provides an advantage that the guidepost of fastening degree at the time of fastening can be easily indicated.

In addition, the target to the base material section may be formed by photogravure or flexography.

It is recommended that the target according to the present invention should be formed by photogravure or flexography.

Further, in the disposable diaper having the fastening front sheet, a constitution may be also made that a shear force determined as a force required to relatively dislocate mutually fastened surfaces of the hook component and the hook receiving component in a direction along both surfaces in a shearing strength test method is 100 g or more, and a peel force determined as a force required to peel off the mutually fastened surfaces of the hook component and the hook receiving component in a direction which intersects with the both surfaces in peel strength test method is 10 g or more.

Although the lower target can be easily observed while the fastening force by the loops is sufficiently maintained by the aforementioned constitution, it is desirable that concrete fastening force is designed so as to have the shear force and the peel force in the aforementioned ranges.

The "shear strength test method" and the "peel strength test method" described in the present invention are defined as follows:

(A) Shear Strength Test Method (a) An entire portion surface having a hook of a hook component 18 which is cut off out of this product is attached to a hook receiving component (front sheet) 15 which is cut into the size of 40 mm×100 mm from a disposable diaper as shown in FIG. 12. In this case, the direction of the hook receiving component 15 to the hook component 18 is the same as in the use of the product, that is, affixing is made so as to allow the longitudinal direction of the hook receiving component 15 in the product condition and the longitudinal direction of the hook component 18 in the product condition to be in parallel with each other.

(b) After that, the base end portion having no hook in the hook component 18 is chucked to a chuck c1 on the tensile testing machine and the unengaged portion in the hook receiving component 15 is chucked to the lower chuck, with a posture allowing the lateral direction in the product condition to be along the longitudinal direction, and the distance cy between the upper chuck c1 and the lower chuck c2 is controlled so as to be 50 mm, and tension is conducted at a tensile speed of 30 mm/min in the shear direction to perform measurement.

(c) The first peak in the obtained chart is read out which is determined to be the shear strength.

(B) Peel Strength Test Method (a) As shown in FIGS. 13A and 13B, the hook receiving component (front sheet) 15 is cut into the size of 40 mm×100 mm from the disposable diaper product. The back side of the hook receiving component 15 is attached with a double-sided adhesive tape to a stainless plate st with the side having the loops to be a front side. The end which is not fixed is fixed in place on the stainless plate st with a craft tape from the surface side.

(b) Next, the entire portion having the hook of the hook component 18 that is cut off out of the product is attached to the front surface of the attached hook receiving component 5. In this case, the direction of the hook component 18 to the hook receiving component 15 is the same direction as in the use of the product, that is, affixing is made so as to allow the longitudinal direction of the hook receiving component 15 in a product condition and the longitudinal direction of the hook component 18 in the product condition to be in parallel with each other. After that, a roller with weight of 2 kg is shuttled back and forth once in the aforementioned direction to engage the hook component 18 with the hook receiving component 15.

(c) Next, these stainless plate st, 15, 18 are fixed in place at the edges of the table tb or the like, the base end portion side having no hook on the hook component 18 is bent from edge of the table tb and is hung up, one end of the craft tape ct is attached to the hung portion, the weight G of 1 kg is mounted on the other end of the craft tape ct, and the load is applied for two seconds.

(d) Next, the load is removed, and the hook receiving component engaged with the hook component is brought into the tensile testing machine which is not shown together with the stainless plate and measurement is performed at a peel-off angle of 90° and a tensile rate of 300 mm/min. This conditions are shown in FIG. 13B.

(e) The maximum value and the minimum value are removed from the obtained chart, each three points of maximum peaks and minimum peaks (total: 6 points) are read out from the remaining peaks, and the average value is found which is determined to be the shear force.

In addition, in the disposable diaper having the aforementioned fastening front sheet, it is preferred that a sound which is generated when the hook component and the hook receiving component which are mutually fastened are peeled off is 15.0 sones or less.

When the fastening force is increased, since the sound at the time of peel-off is excessive and is liable to be noticeable, it is preferred that a peel-off sound is designed so as to stay within the aforementioned range.

Here, the loudness of the sound (sone) in the present invention is a value which is found by assigning a value P (phone) measured with a general noise meter when a peel-off is performed into the following equation (1).

$$S=2^{(P-40)/10} \quad (1)$$

In addition, for the hook receiving component, a breathability by JIS-P-8117: Gurley method may be also 9.0 sec/100 ml or more.

When the breathability stays within the range, a sufficient breathability can be secured even if the hook receiving component is provided on the belly side, a wearer hardly feels unpleasant. When the breathability is also given to a non-liquid permeable sheet, the breathability is not damaged in the portion of the fastening front sheet.

For the hook receiving component, the moisture permeability by JIS-L-1099: MVTR method may be also 500 g/m$^2$·d or more.

When the moisture permeability stays within the range, a sufficient moisture permeability can be secured even if the hook receiving component is provided on the belly side, a wearer hardly feels unpleasant. When the moisture permeability is also given to a non-liquid permeable sheet, the moisture permeability is not damaged in the portion of the fastening front sheet.

Gigging treatment may be performed on the surface of the hook receiving component having the loops.

Performing the gigging treatment allows the loops to be drawn out and to be untangled, thereby an engaging force with the hook component is improved. In this case, although the target becomes difficult to be observed a little than the one on which gigging treatment is not performed, since it is more significantly observed than a conventional one where the filament yarn on which crimp treatment is performed is used and the fastening force is improved by gigging treatment, easiness of looking the target can be improved by lowering the loop density, thereby an affection upon the easiness of looking the target by gigging treatment can be countervailed.

Further, each of the loops may be formed of a non-crimp treated straight or slowly curved filament yarn.

The material of the filament yarn may be made of nylon.

A straight or slowly curved filament yarn where a crimp-treatment is not performed is excellent in visibility. In addition, when the material of the filament yarn is of nylon, the fastening force of the hook component is excellent.

According to the third aspect in the present invention, a disposable diaper comprises a fastening piece mounted at both ends on a rear side of the disposable diaper, a hook component on a fastening surface of the fastening piece, and an external sheet which forms a back surface of the disposable diaper and is made of a non-woven cloth, the hook component of the fastening piece being engageable at an arbitrary position on a surface of a non-woven external sheet when wearing the disposable diaper, wherein a target printing for printing a guidepost of a position where the hook component of the fastening piece is fastened is performed at least on either the non-woven external sheet or a sheet thereunder to allow the guidepost to be observed from outside.

According to the disposable diaper like this, since there is provided the target printing as the guidepost of the position where the hook component of the fastening piece is fastened, the fastening work is easy as it can be observed from the outside.

In addition, the disposable diaper like this may have a non-liquid permeable sheet which substantially prevents a liquid from permeating inside the non-woven external sheet, the target printing being performed on the non-liquid permeable sheet which substantially prevents the liquid from permeating.

By this arrangement, the flow of a body fluid absorbed by an absorbent component into the back side can be suppressed by the non-liquid permeable sheet which does not substantially permeate the liquid. A printing technology to a usual plastic sheet can be adopted as it stands to performing the target printing on this non-liquid permeable sheet which does not substantially permeate the liquid, for example, a polyethylene-made non-liquid permeable sheet which does not substantially permeate the liquid, and the printing can be beautifully and clearly observed from the outside.

This target printing may be performed on the body peripheral portion in a front side.

In addition, a longitudinal length of the target printing is performed may be 10 to 400 mm and a length in a body peripheral direction thereof may be 50 to 500 mm.

The target printing may be performed and constituted so as to show a plurality of different fastening positions in the body peripheral direction.

When this is done, it is possible to select the fastening position.

In addition, the target printing may be performed with photogravure or flexography.

In addition, the non-liquid permeable sheet which substantially prevents the liquid from permeating inside the non-woven external sheet may be provided, and a target printing may be-performed on a skin side of the non-liquid permeable sheet which substantially prevents the liquid from permeating with either a water-soluble ink or a water-insoluble ink or both of them.

Although the target printing may be performed with a water-insoluble ink, it is preferable that a water-soluble ink is used. In case of using the water-soluble ink, the water-soluble ink is dissolved as the absorbed quantity of a body fluid is increased. Thereby, the target printed surface is dimmed, so that, on the contrary, a wearer can judge the limitation of the absorbed quantity due to a large quantity of the body fluid and when the disposable diaper should be replaced with a new one. Both a water-soluble ink and a water-insoluble ink can be used by partially dividing use areas.

A constitution may be so made that gigging treatment is performed at least on a portion corresponding to a portion on which the target printing is performed in the non-woven cloth external sheet.

The fastening property of the hook component is increased by gigging the portion corresponding to the target printing.

In addition, according to the disposable diaper of the third aspect in the present invention, the disposable diaper comprises the non-liquid permeable sheet which substantially prevents the liquid from permeating inside the non-woven external sheet, the target printing being performed on the non-liquid permeable sheet which substantially prevents the liquid from permeating, wherein an emboss of 2 to 30% per unit area is performed at least on a portion corresponding to a portion on which the target printing is performed from an external surface of the non-woven cloth external sheet.

In the portion corresponding to the target printing, in a process where the fastening of the hook component is repeated, a peel-off occurs between the non-woven cloth external sheet and the non-liquid permeable sheet which does not substantially permeate the liquid and gigging occurs, so that an attractive appearance and repeated fastening property are damaged. Therefore, the non-woven cloth external sheet and the non-liquid permeable sheet which does not substantially permeate the liquid can be bonded and gigging of the non-woven cloth external sheet can be prevented by embossing. This embossing can be performed not only on the portion corresponding to the target printing but also on other portions, for example on the entire area.

In addition, the non-liquid permeable sheet which substantially prevents the liquid from permeating inside the non-woven external sheet may be provided, wherein the non-woven cloth external sheet and the non-liquid permeable sheet which substantially prevents the liquid from permeating may not be entirely bonded with a hot-melt adhesive or heat bonding and bonding portions may be spaced out at least on the portion corresponding to a portion on which the target printing is performed.

When the non-woven cloth external sheet and the non-liquid permeable sheet which does not substantially permeate the liquid are bonded, for example, although it is also considered that bonding is performed on an entire area or a comprehensively big area with a hot-melt adhesive, it can not be avoided that the hot-melt adhesive seeps out on the non-woven cloth external sheet.

Therefore, in case of adopting a form that the non-woven cloth external sheet and the non-liquid permeable sheet which does not substantially permeate the liquid are bonded with a hot-melt adhesive, when it is a form that the entire bonding is not performed with the hot-melt adhesive and the bonded area is spaced out, seepage does not occur. As this concrete example, for example, it is desirable that the area is spaced out in a stripe.

On the other hand, a form that the non-woven cloth external sheet and the non-liquid permeable sheet which does not substantially permeate the liquid are bonded with heat bonding can be also adopted, in this case, since bonding is performed with heat bonding, the bonding can be performed with no seepage of a hot-melt adhesive.

In any form, gigging of the non-woven cloth external sheet can be prevented in at least the portion corresponding to a portion on which the target printing is performed with the aforementioned bonding.

According to the fourth aspect in the present invention, a disposable diaper comprises a fastening piece mounted at both ends on a rear side of the disposable diaper, a hook component on a fastening surface of the fastening piece, and an external sheet which forms a back surface of the disposable diaper and is made of a non-woven cloth, the hook component of the fastening piece being engageable at an arbitrary position on a surface of a non-woven external sheet when wearing the disposable diaper, wherein a shear force between the fastening surface of the fastening piece and the surface of the non-woven external sheet which are mutually fastened is 50 g or more, and a peel force between the fastening surface of the fastening piece and the surface of the non-woven external sheet which are mutually fastened is 10 g or more.

The defined shear force and peel force allow the disposable diaper to have a definite fastening property.

In addition, in the disposable diaper in the third and fourth aspects according to the present invention, it is preferred that a sound which is generated when the fastened surface of the fastening piece and the surface of the non-woven cloth external sheet that are mutually fastened are peeled off is 12.0 sones or less.

When this is arranged, a wearer does not feel unpleasant since the sound when the portions are peeled off is small.

According to the fifth aspect in the present invention, a disposable diaper comprises a non-liquid permeable sheet which substantially prevents a liquid from permeating inside an external sheet, a fastening piece protruded laterally at both ends on a rear side of the disposable diaper, a hook component on a fastening surface of the fastening piece and the external sheet of the disposable diaper which is made of a non-woven cloth, the hook component of the fastening piece being engageable at an arbitrary position on a surface of the non-woven external sheet when wearing the disposable diaper, wherein a fastening receiving front sheet having the hook receiving component detachably engaged with the fastening piece is not provided, and the non-liquid permeable sheet which substantially prevents the liquid from permeating has a breathability.

Although as a non-liquid permeable sheet which does not substantially permeate the liquid, the non-liquid permeable sheet can be formed by a single polyethylene sheet or a poly laminate non-woven cloth internal surface side of which comprises a polyethylene sheet or the like and an external surface side of which comprises a non-woven cloth, stuffiness takes place. Thus, it is preferable to give the breathability to the non-liquid permeable sheet which does not substantially permeate the liquid to prevent stuffiness. As this method, a form that a number of fine needle holes are formed on a single polyethylene sheet or on the poly laminate non-woven cloth, and an embodiment that the sheet is formed by a high-density non-woven cloth can be taken up. It is preferable that a sheet to which a moisture permeability is given besides this breathability is used.

In this case, a target printing with printing thickness of 10 to 50 μm as the guidepost of a position where the hook component of the fastening piece is fastened may be performed at least on either the non-liquid permeable external sheet or a sheet thereunder so as to allow the guidepost to be observed from outside.

In addition, an air permeability between a skin side of the non-liquid permeable sheet which substantially prevents the liquid from permeating and the surface of the external sheet at a position where the hook component of the fastening piece is fastened may be 5 cc/10 mini or more.

In the disposable diaper in the fifth aspect according to the present invention, the target printing may be performed on the body peripheral portion in the front side.

In addition, in the disposable diaper in the third to the fifth aspects according to the present invention, the non-liquid permeable external sheet may comprise a fiber material of single fiber or long fiber, and the denier number thereof may be 2.5 d or less.

When this is arranged, a feel on the fibers is excellent and it can give a feel like that of a cloth. In addition, the fastening property of the hook component is excellent.

BRIEF DESCRIPTION OF THE DRAWINGS

FIG. 14 is a major-portion longitudinal cross-section in a condition where a fastener tape is temporarily fixed in place;

BEST MODE FOR CARRYING OUT THE INVENTION

Figure 1:
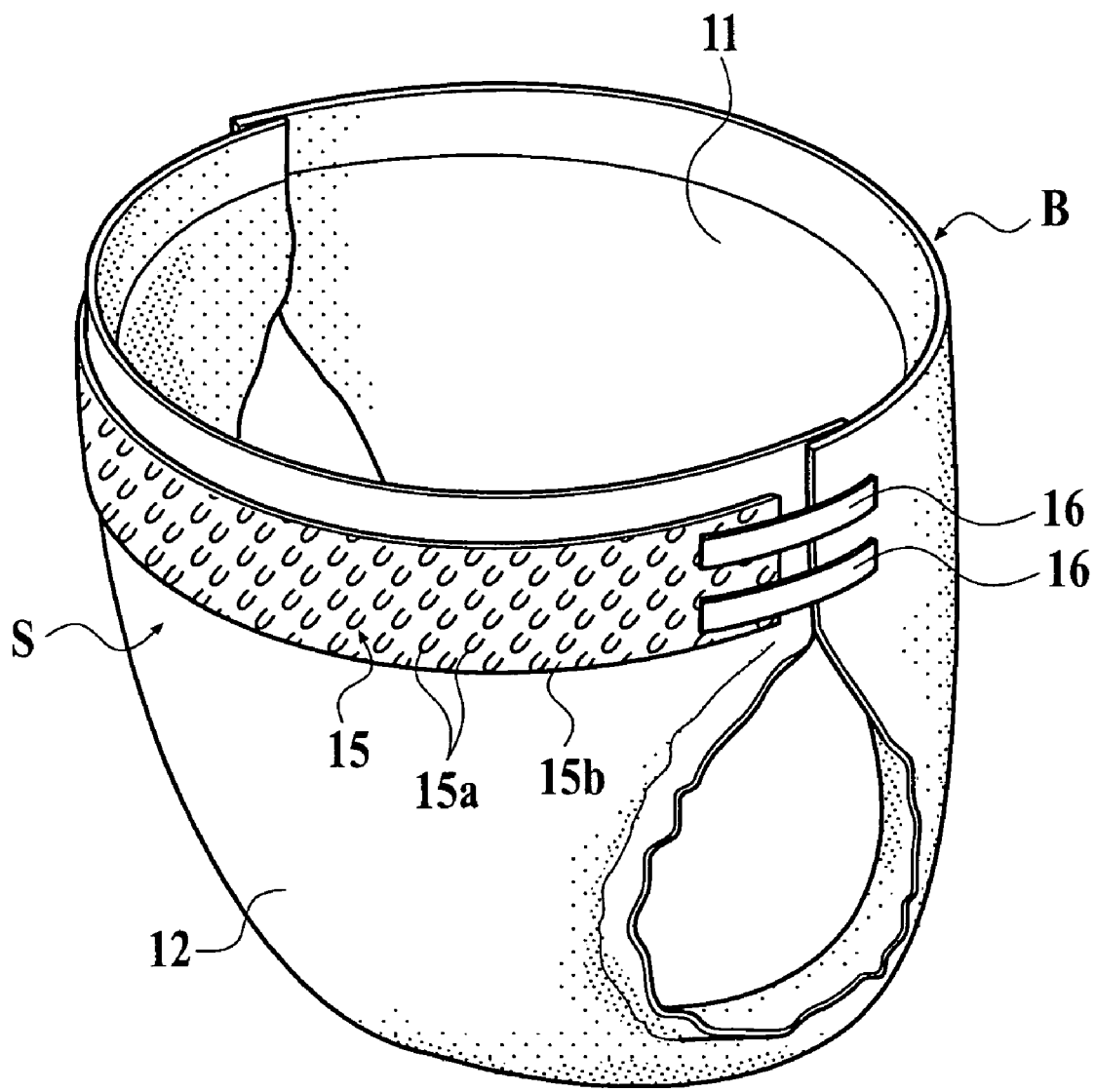
FIG. 1 is a perspective view showing a wearing condition of the disposable diaper in the first embodiment according to the present invention.

The present invention is further described in detail referring to the embodiments as shown in the drawings below.

FIG. 1 to FIG. 4 show the disposable diaper in the first embodiment according to the present invention. The body of the disposable diaper comprises the basic constitution components such as a liquid-permeable top sheet 11 made of a non-woven cloth or the like on the surface side (a surface which directly contacts a human skin) and a non-liquid permeable back sheet 12 on the back side comprising a polyethylene sheet or the like, more preferably, a poly laminate non-woven cloth internal surface side of which comprises a polyethylene sheet or the like and an external surface side of which comprises a non-woven cloth, a peripheral portion is left as a flap portion, and an absorbent body 13 comprising a floccular pulp or the like interposed therebetween.

Here, it is desirable that the non-liquid permeable back sheet 12 comprising a poly laminate non-woven cloth uses the one to which an breathability and a moisture permeability are given by forming a number of fine needle holes therein.

One or plurality of elastic expansion members 14A are provided at leg periphery portions adjacent to the absorbent body 13 if required. Elastic expansion members for front and back leakage prevention 14B are provided at the front and back ends if required. Although for the form as shown in the figure, one or a plurality of elastic expansion members 14A are provided at the leg periphery portions adjacent to the absorbent body 13 as a plane gather, more preferably, it is provided as barrier cuffs (called rising cuffs).

Although the disposable diaper of this kind is publicly known, in the present invention, the hook receiving sheet (entanglement receiving sheet) 15 comprising the hook receiving component where a number of 15a protrudes into a base material section 15b is fixed in place at the external surface of the belly S by the non-liquid permeable back sheet 12 as a so-called front sheet. However, for loop 15a in the hook receiving sheet 15 as shown in FIG. 1, the size and layout are decided for the sake of visibility, and there is no correlation with the range of the present invention later described.

On the other hand, one of the other components of the hook and loop fastener is fixed in place at both side portions on the back B side. In the example, the both side portions on the back B side comprise the back sheet 12 and the top sheet 11, a main tape member 16 is projected outwardly from the side edge to the surface of the back sheet 12 and is fixed in place, for example, by an adhesive layer 16A, and a sub tape member 17 is provided between the surface of the top sheet 11 and the internal surface side of the main tape member 16 which strides over the side edge, for example, the sub tape member 17 is provided with both ends fixed in place by the adhesive layer 17A.

A hook sheet 18 is fixed, for example, by the adhesive layer 18A on the internal surface side of the main tape member 16 where the sub tape member 17 does not exist. The hook sheet 18 comprises the hook component of the hook and loop fastener.

The hook sheet 18 is formed by implanting a number of hook pieces 18a on a base material section 18b, and the hook piece 18a is detachably engaged with the loop 15a. In addition, the tip of the hook sheet 18 is left as a knob section by preferably providing the same in the internal side from the tip of the main tape member 16.

Figure 4:
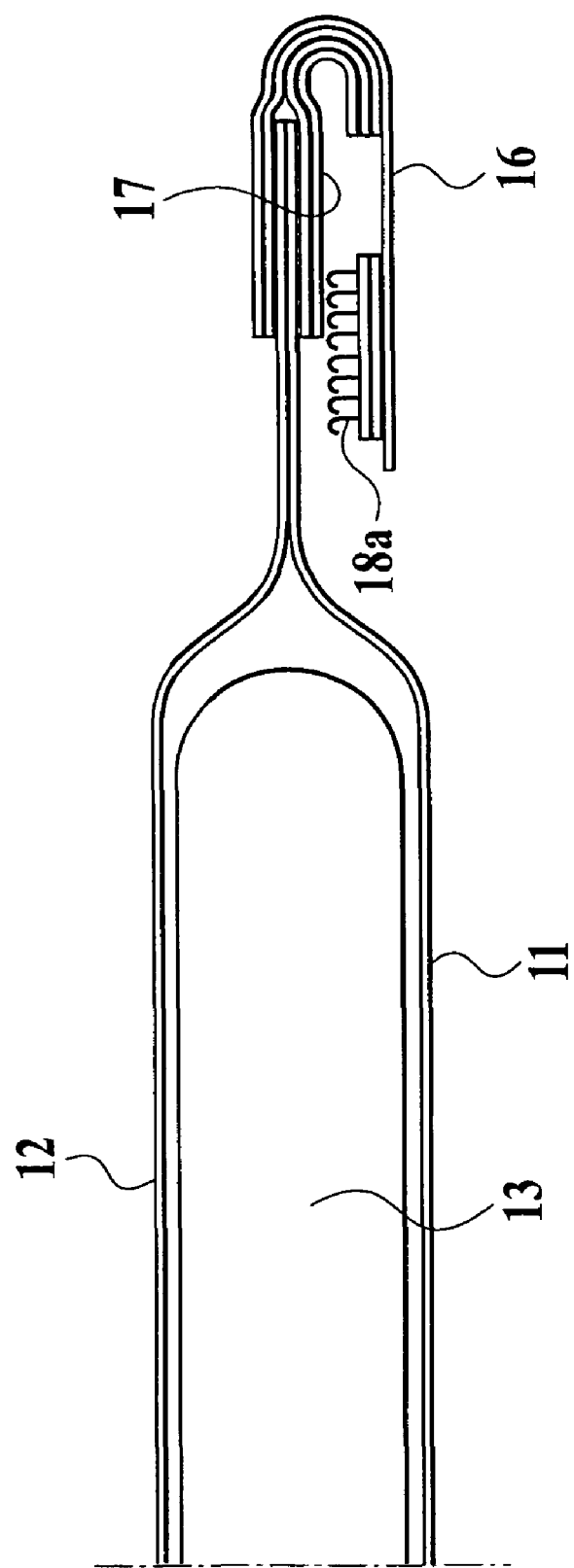
FIG. 4 is a major-portion longitudinal cross-section in a condition where a fastener tape is temporarily fixed in place.
Figure 5:
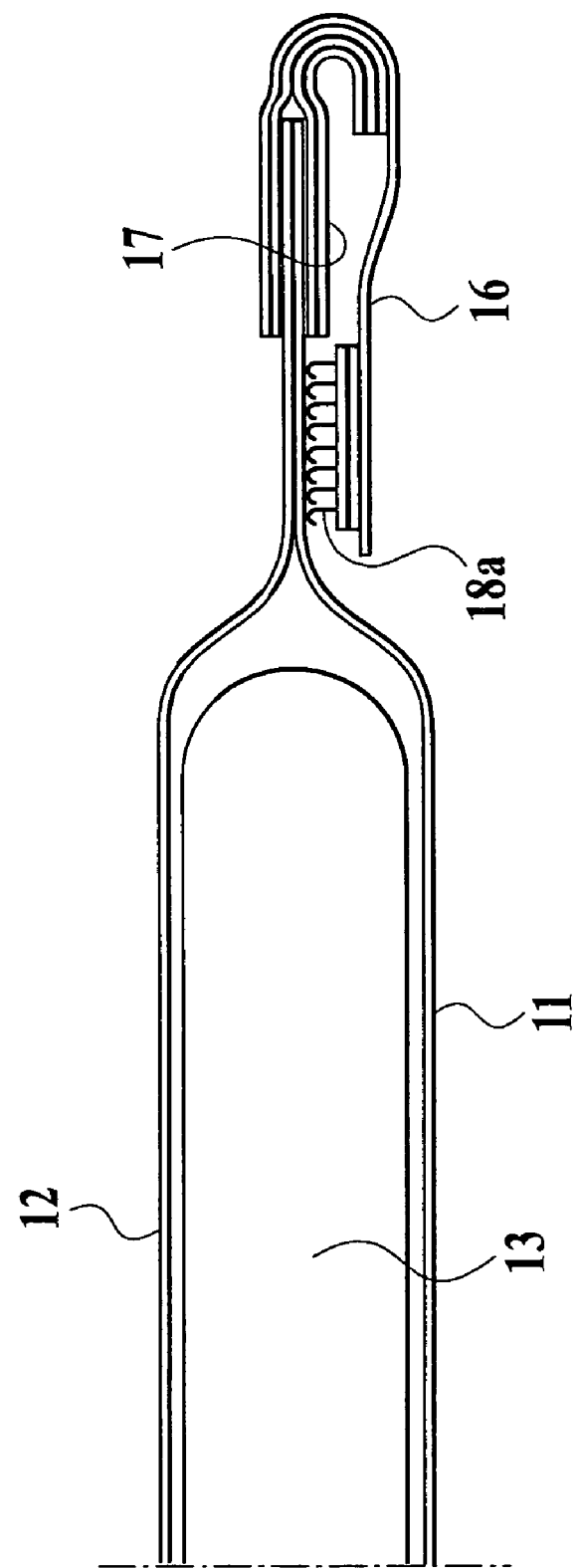
FIG. 5 is a major-portion longitudinal cross-section in a condition where a fastener tape in another example is peeled off.

On the other hand, as shown in FIG. 4, the main tape member 16 is folded inside the product when the disposable diaper is not put on. In this case, the hook sheet 18 is peelably engaged with the fibers of the top sheet 11 comprising a non-woven cloth at a position exceeding a part of the sub tape member 17 or the entire sub tape member 17 as shown in FIG. 5. In order to further reduce the number of the constituting parts, as shown in FIG. 14, it is also possible by using only the main tape member 16 to fix only the base end portion thereof and the portion corresponding to the side edge of the back sheet 12 to the back sheet 12 through the adhesive layers n1, n2, and to fix the main tape member 16 in a state of being folded inwardly inside the product, when the disposable diaper is not put on, by an adhesive layer n3 which is formed in an intermediate area on the tip side ahead of a portion of the hook piece 18a in the main tape member 16.

In the relevant disposable diaper, after the main tape members 16 having the hook sheet 18 and the sub tape member 17 are mounted on the body of the disposable diaper, as shown in FIG. 4, the main tape member 16 is folded inside the disposable diaper, and the hook sheet 18 is engaged with the top sheet 11 comprising a non-woven cloth by entangling the same therewith at a position exceeding a part of the sub tape member 17. Then, manufacturing processes are further performed, and the products are shipped after packing.

When the disposable diaper is put on, the tip of the main tape member 16 is picked up, the hook sheet 18 is peeled off out of the top sheet 11, the extended portion is brought into the belly side S, and the hook sheet 18 is superimposed on the hook receiving sheet 15. This superimposition allows each hook piece 18a to entangle with each loop 15a to perform bonding back and forth of the disposable diaper.

When looking whether or not there is emiction or repeating mounting for adjustment, the extended portion of the hook sheet 18 may be peeled off from the hook receiving sheet 15 and re-bonding may be performed.

In the aforementioned embodiment, although the hook sheet 18 is fixed in place at the main tape member 16 by the adhesive 18A, the base material section 18b of the hook sheet 18 can be also fixed in place at the main tape member 16 with heat bonding or the like without using the adhesive layer 18A.

Figure 2:
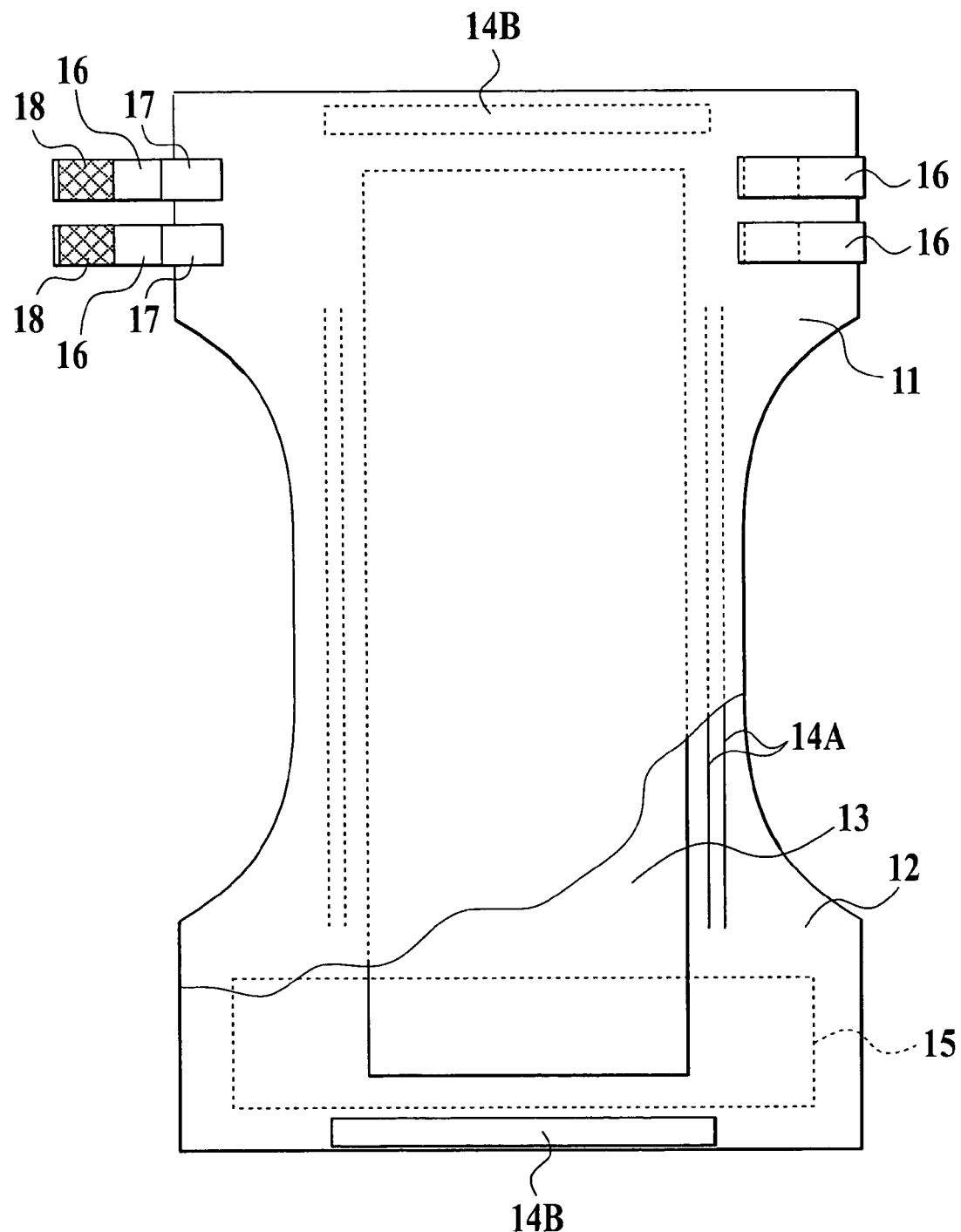
FIG. 2 is a product development of this disposable diaper.
Figure 3:
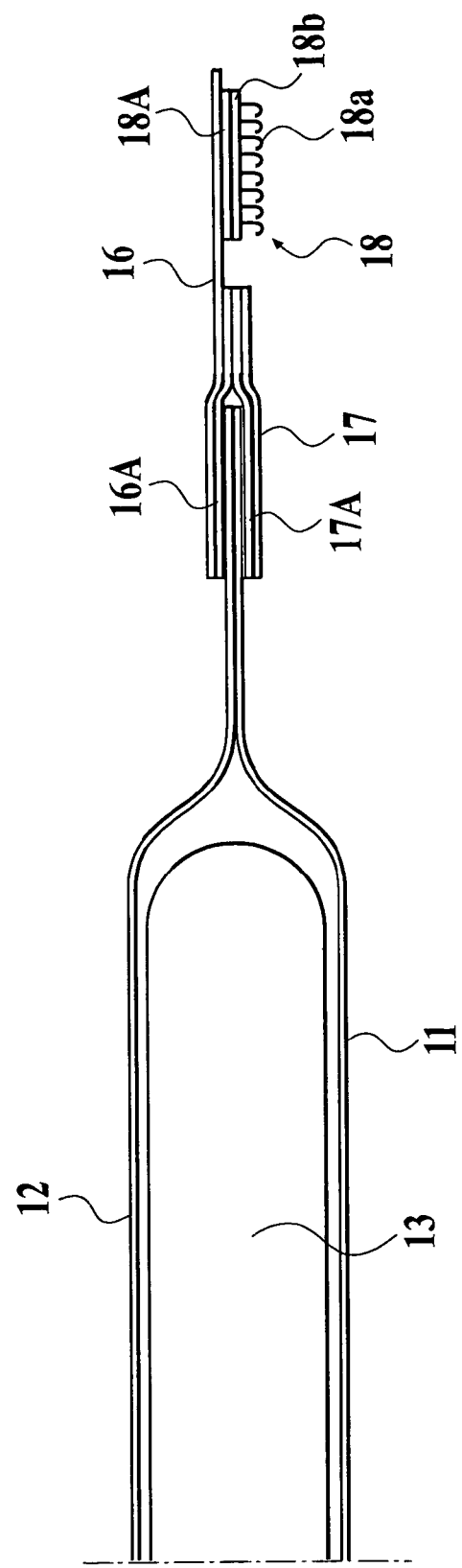
FIG. 3 is a major-portion longitudinal cross-section in a condition where a fastener tape is peeled off.
Figure 6:
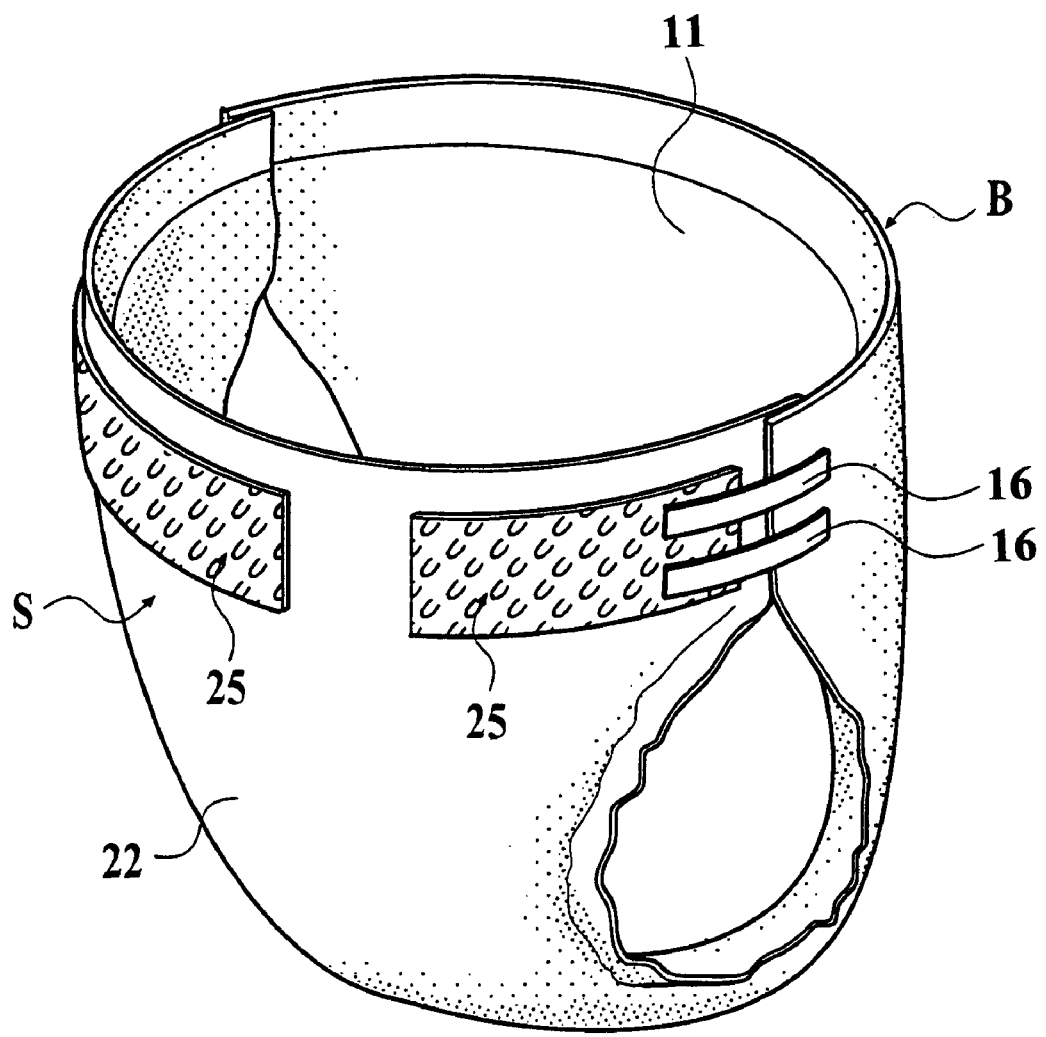
FIG. 6 is a perspective view showing the wearing condition of the disposable diaper in the second embodiment according to the present invention.

A plurality of hook sheets 18 can be also provided along the longitudinal direction of the main tape member 16. As shown in FIG. 1 and FIG. 2, although each two of the fastener tapes of the main tape members 16 having the hook sheet 18 and the sub tape member 17 are provided on one both-side portions of the disposable diaper, each one or each three or more may be provided depending upon the bonding strength (or depending upon applications such as ones for infants or the like). In addition, as shown in FIG. 6, the hook receiving sheet 25 may be disposed separately corresponding to belly sides.

Figure 7:
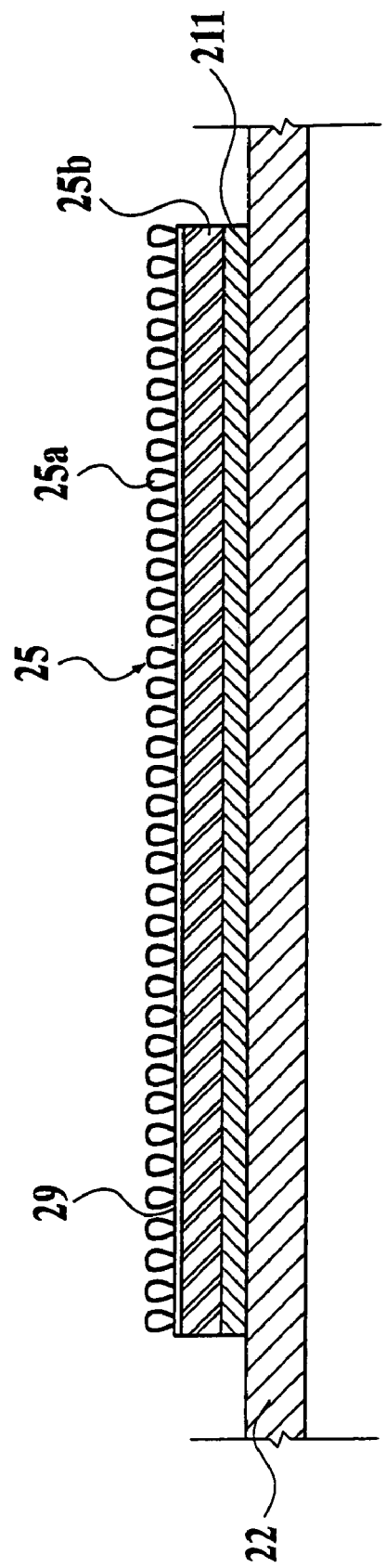
FIG. 7 is a longitudinal cross-section of the front sheet.

As aforementioned, in the present invention, as a cross-section is shown in FIG. 7, the hook receiving sheet 25 forming the hook receiving component where a number of loops 25a are projected on the surface of the base material section 25b is fixed in place on the non-liquid permeable back sheet 22, for example, with a hot-melt adhesive 211. In this case, as shown in the figure, it is desirable that after the target is directly arranged on the surface of the base sheet comprising the base material section 25b with publicly known printing means such as photogravure or flexography, the loops are fixed in place on the surface with a hot-melt adhesion or the like. The target may be also arranged on the back side, in this case, the base material sheet per se is formed of a transparent or translucent material. It is preferred that for this base material sheet 25b, the thickness is 25 μm or less including the printed thickness and it is desirable that the material is polyethylene.

Figure 8:
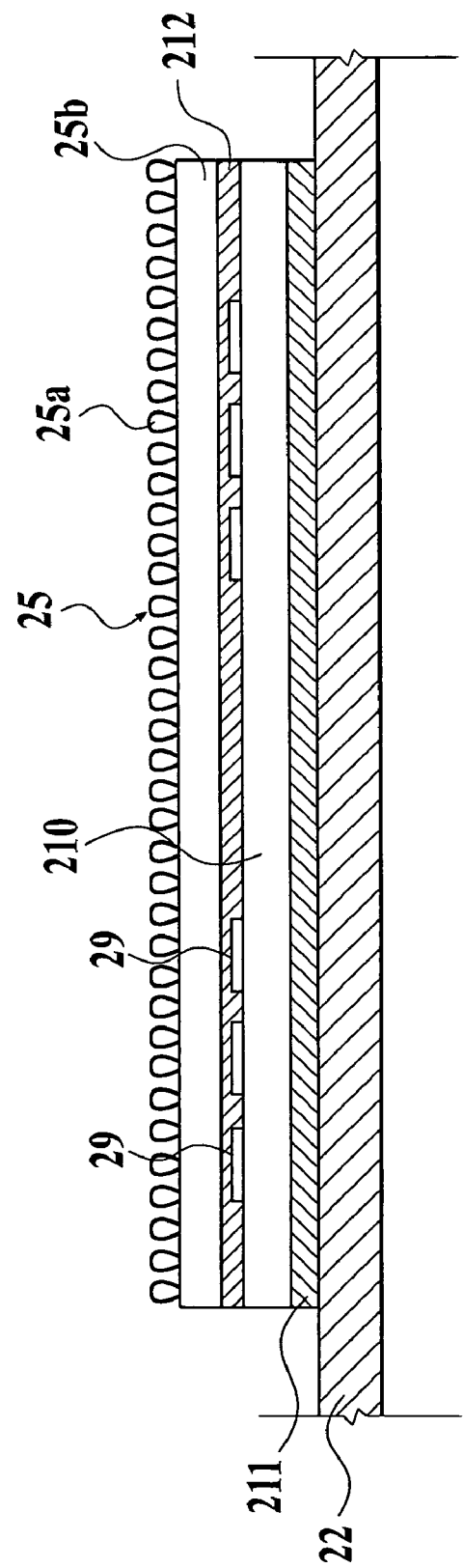
FIG. 8 is a longitudinal cross-section of the front sheet.

In addition, as shown in FIG. 8 as a cross-section, in place of directly fixing in place the hook receiving sheet 25 on the non-liquid permeable back sheet 22, at a position where the hook receiving sheet 25 should be fixed in place, the printed film 210 where the target 29 for the fastening position of the hook sheet 18 is printed on the external surface is fixed in place at the liquid-permeable back sheet 22, for example, with the hot-melt adhesive 211. The hook receiving sheet 25 is superimposed and integrated on the printed film 210 with heat bonding (a heat bonded layer is shown by reference numeral 212), and the hook receiving sheet 25 may be also formed of a transparent or translucent material so as to allow the target to be observed from the outside. In this case, the printed film 210 also comprises the base portion according to the present invention. Thus, the target 29 can be observed from the outside through the hook receiving sheet 25, and the fastening position of the hook sheet 18 can be selected corresponding to the target 29.

Figure 9:
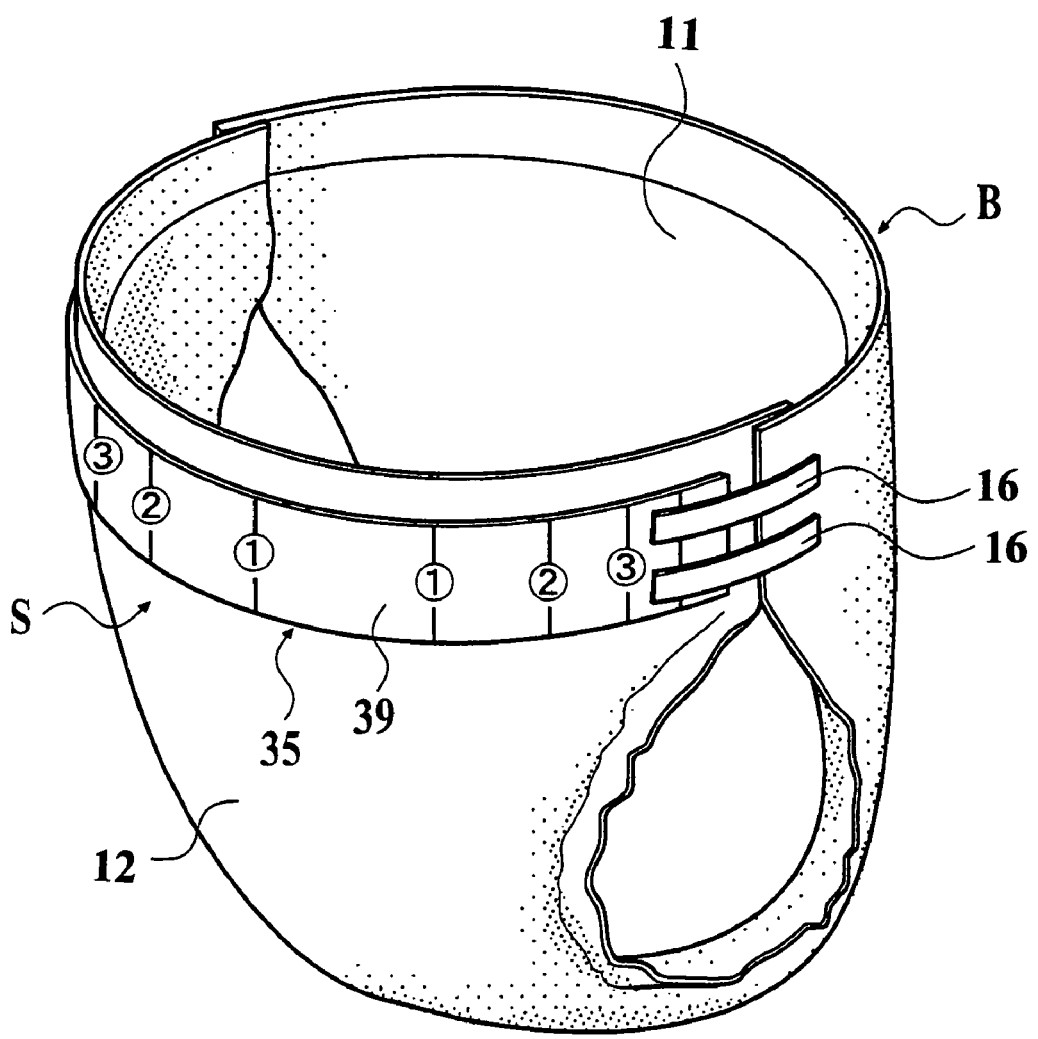
FIG. 9 is a perspective view showing the wearing condition of the disposable diaper in the third embodiment according to the present invention.

The target 29 can be indicated in a number, a mark, a color-coded band, a line or the like, particularly, it is desirable that with these symbols, as shown in the third embodiment according to the present invention in FIG. 9, the target 39 having a color-coded striped design is formed so as to show a plurality of different fastening positions in a body peripheral direction. The color-coding and loop are omitted for the sake of visibility of the drawing in FIG. 9. However, in the present invention, a number of loops are provided on the hook receiving sheet 35 as mentioned below.

Figure 10:
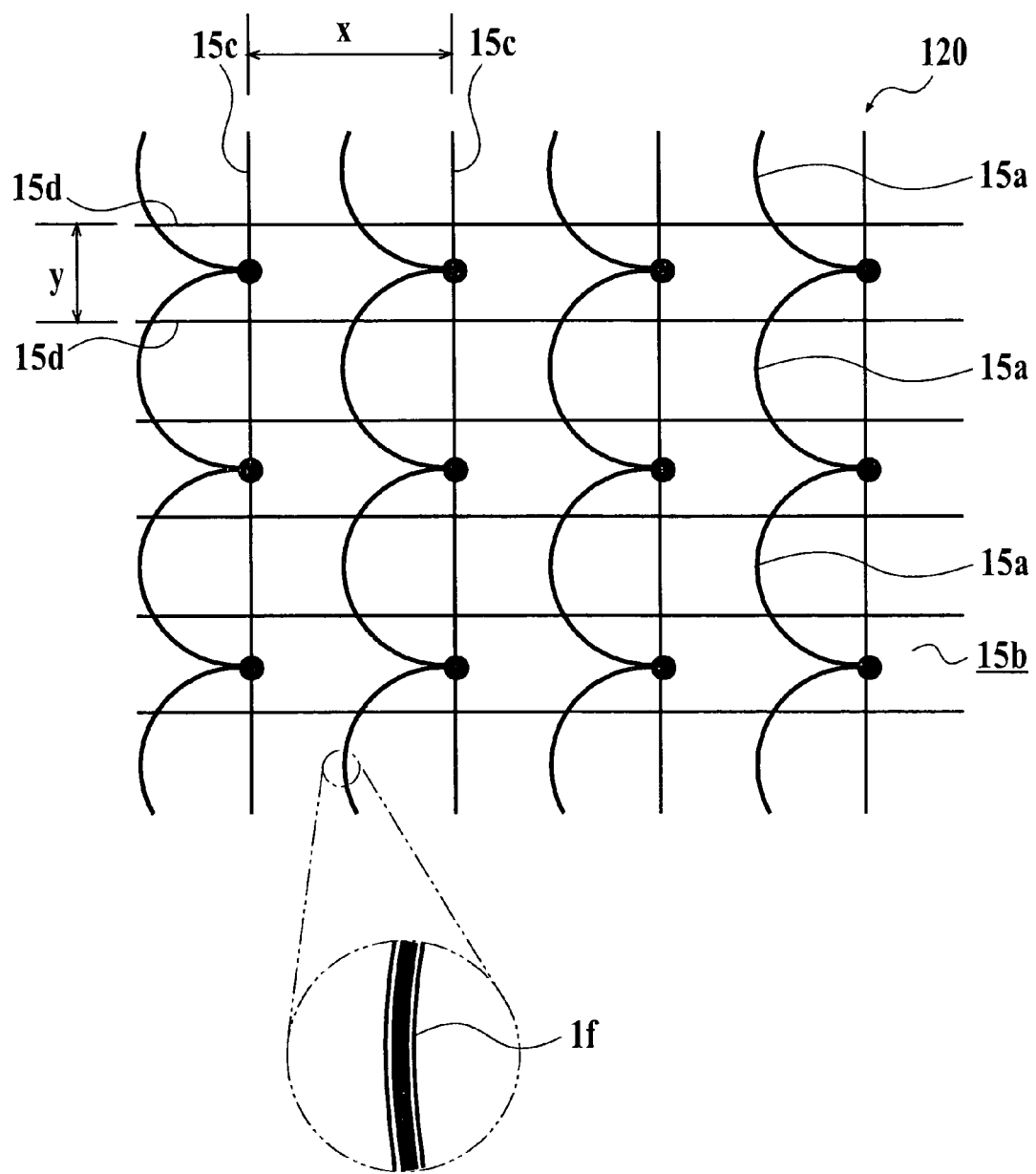
FIG. 10 is a major-portion enlarged plan view of the front sheet according to the present invention.
Figure 11:
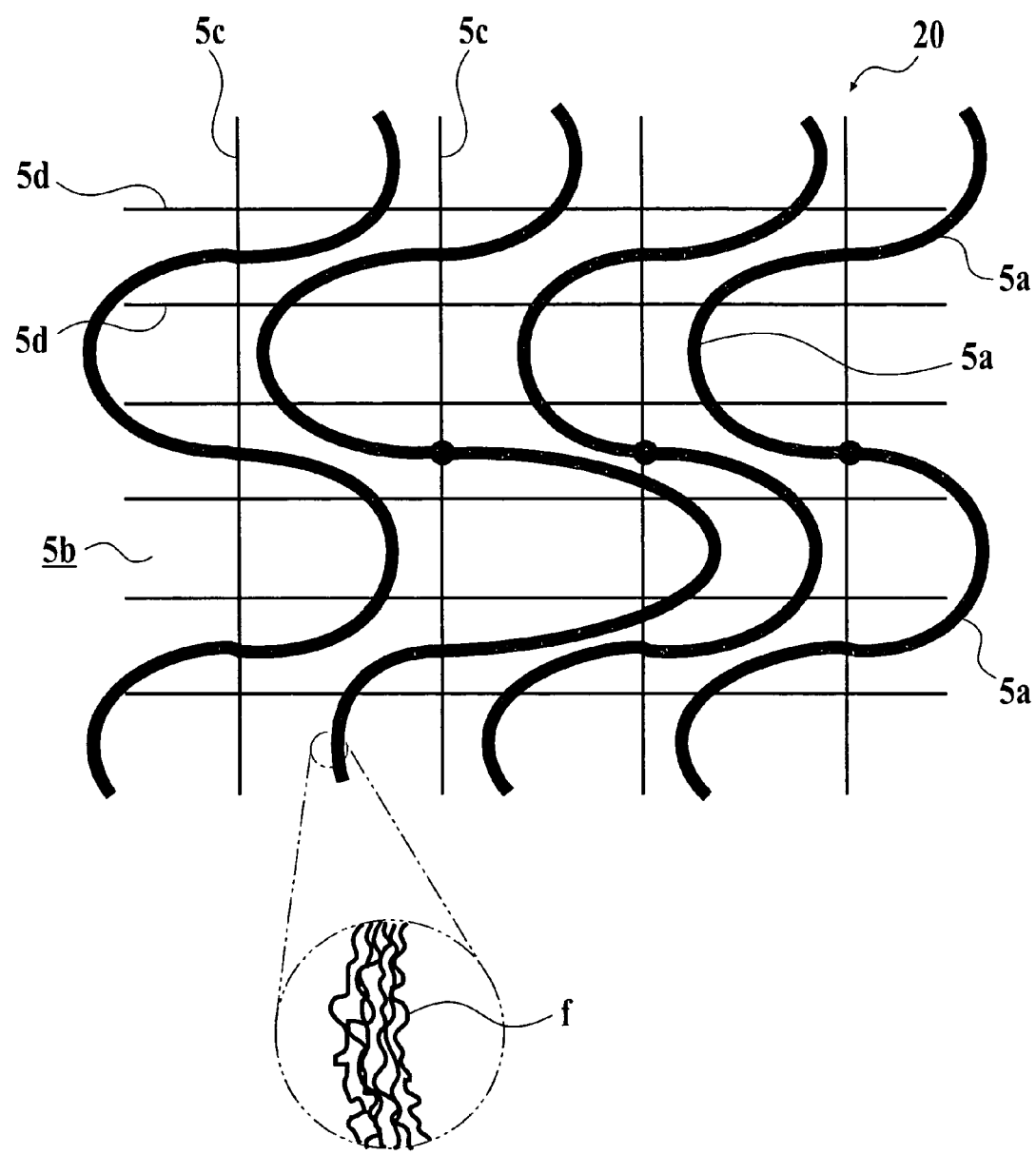
FIG. 11 is a major-portion enlarged plan view of a conventionally used front sheet.

And, particularly in the present invention, as the plane is shown in FIG. 10, all loops 15a, 15a (or 25a, 25a), . . . are formed of non-crimp treated straight or slowly curved filament yarn. When a filament yarn comprising a filament with almost the same size as in a conventional product is used, the thicknesses of almost all the loops are about 200 μm or less although it cannot be said unconditionally. In the present invention, by using the relevant straight or slowly curved filament yarn, as it is clear when compared with the comparison diagram of a conventional product, the masking area by the loops 15a, 15a (or 25a, 25a), . . . is significantly small, and the targets 29, 39 of the base portion 15b (or 25b) can be easily observed irrespective of the existence of the loops 15a, 15a (or 25a, 25a), . . . .

However, when only this is provided, the engagement force with the hook is weak since a crimp-treatment is not performed, it is desirable that the density of the number of the loops 15a, 15a (or 25a, 25a), . . . is determined to be 10 to 60, preferably to be 30 to 60 pcs/cm$^2$ and more preferably to be 40 to 50 pcs/cm$^2$. When the density of the number of the loops 15a, 15a (or 25a, 25a), . . . stays within the relevant range, the lower target 29 can be easily observed contrary to damaging the easiness of looking the target as mentioned above.

In addition, as shown in the drawings, when using the hook receiving component comprising the base portions 15b (25b) having the targets 29, 39 which can be observed from the surface side and the grid-net body so constituted as to allow a number of loops 15a (25a) fixed on the surface of the base portion 15b (25b) to be swollen and extruded, when the entire grid-net body (that is, all of longitudinal fiber portion 15c, lateral fiber portion 15d and loop 15a) are formed of a non-crimp treated straight or slowly curved filament, the targets 29, 39 of the lower base portions 15b (25b) are easily observed. In this case, by setting the density of the number of the loops 15a, 15a, . . . (25a, 25a, . . .) at the aforementioned ranges and setting the longitudinal fiber portion spacing y at 1.5 mm or less, preferably at 0.7 to 1.3 mm and the lateral fiber portion spacing x at 3.0 mm or less, preferably at 1.5 to 1.8 mm in the grid-net body 120, the lower target 29 (39) is easily observed (instead of damaging the easiness of looking at the target as described above). In this case, it is desirable that the target range of the grid-net body is 25.0 to 34.0 g/m$^2$.

Here, for the filament yarn, fine filament 1f of ten and several pieces are bundled as the enlarged view shows, although all the publicly known materials such as polyethylene terephthalate (PET) and nylon can be used, nylon is particularly desirable. It is desirable that the color of the filament yarn is white, translucent or transparent.

Further, in order to allow the targets 29, 39 of the base portions 15b (25b) to be easily observed, when the hook receiving component is observed from the top, it is preferred that the hook receiving component has a form in that the loops 15a (25a) of 60 to 70% or more and preferably 80 to 90% or more are seen as if they were swollen and extruded in the predetermined same directions (swollen and extruded to the left side relative to the longitudinal direction in the figure) as is shown in the figures. For that reason, it is desirable that the length of one loop 15a (25a) is determined to be 3 mm or less, preferably to be 2 mm or less, so as not to allow the loops to be irregularly distorted.

In addition, as the final guidepost for the easiness of looking the target, there is the light transmittance of the hook component as a simple body, it is preferable that the light transmittance in the present invention is 60% or less.

In the case shown in the drawings, the loops 15a (25a) are fixed with the grid-net body in place at the base portion 15b (25b), for example by hot-melt adhesive.

In this case, although rubber series, styrene series and polyurethane series adhesive can be used as the hot-melt adhesive to be used, when the polyurethane series adhesive is used among them, a luster is reduced and the target is more easily observed. It is preferred that the spread of the relevant adhesive is 3.5 g/m$^2$ or more, preferably 4.0 to 5.0 g/m$^2$.

On the other hand, as mentioned above, although by increasing the density of the number of the loops 15a (25a), the fastening force (the engagement force) may not be damaged, it is preferred that each of the aforementioned factors is set so as to allow the shear force by the aforementioned shear strength test method to be 100 g or more and allow the peel force by the aforementioned peel strength test method to be 10 g or more as the final guidepost of this fastening force.

In addition, in the present invention, gigging treatment is performed on the surface of the hook component having the loops 15a (25a), and the loops 15a (25a) are slightly drawn, so that the loops are unfastened. Thus, the engagement force with the hook component can be improved. In this case, since the fastening force is improved, the easiness of looking at the target can be improved by lowering the loop density to countervail the affection upon the easiness of looking at the target by the gigging treatment.

As other additional treatments, to the hook receiving component according to the present invention, for example, by dispersedly providing a number of fine watermarked holes or depressed holes (not shown), it is preferred that the breathability by JIS-P-8117: Gurley method is 9.0 sec/100 ml or the moisture permeability by JIS-L-1099: MVTR method (calcium chloride method) is 500 g/m$^2$·d.

As is clear from the foregoing, according to the first to the third embodiments in the present invention, for using a hook and loop fastener tape as the fastening means of the disposable diaper, the target of the base portion of the hook receiving component is easily observed although the target is masked with the loops.

Figure 15:
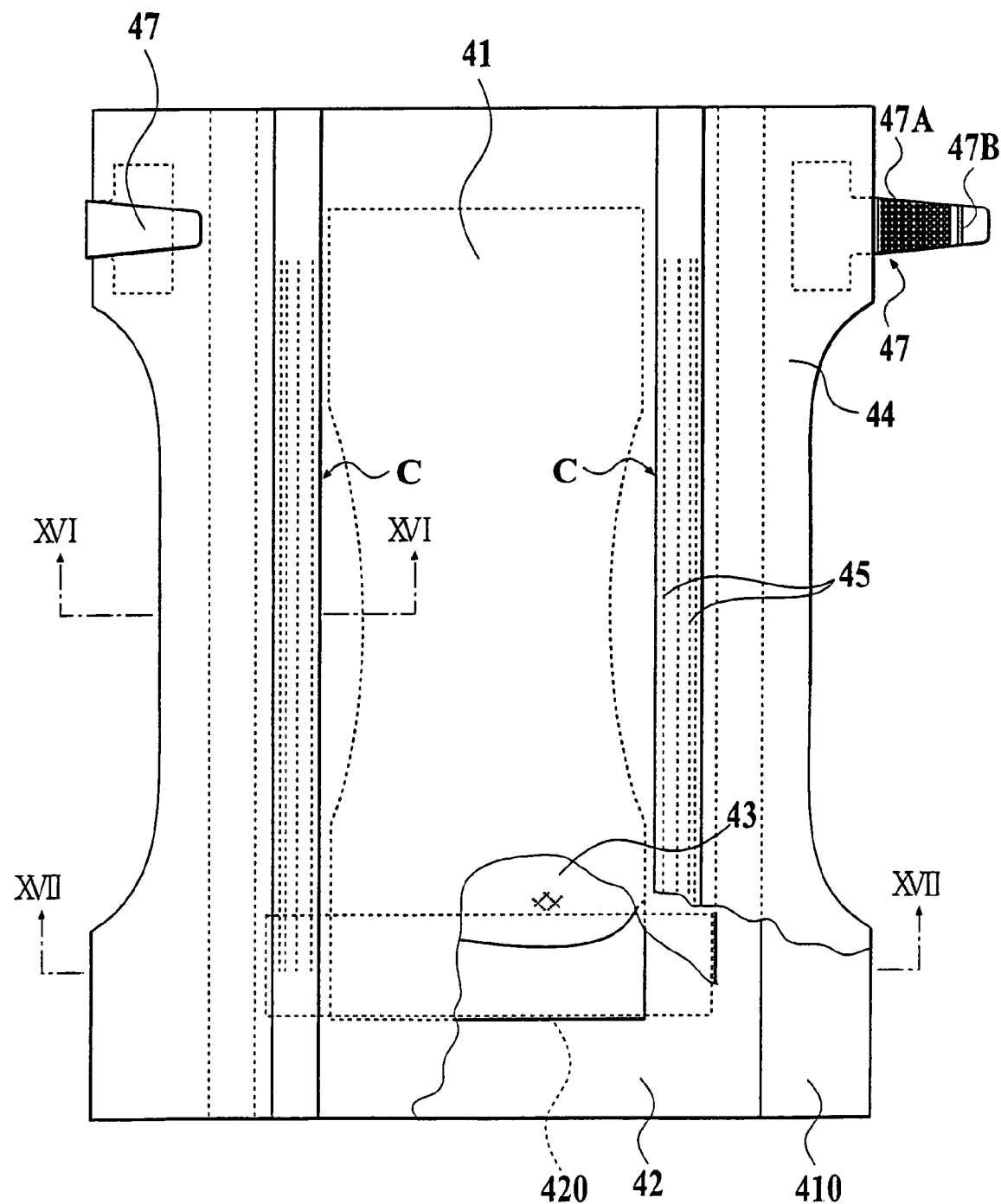
FIG. 15 is a partially exploded plan view showing the developed condition of the disposable diaper in the fourth embodiment according to the present invention.

FIG. 15 shows the fourth embodiment of the disposable diaper according to the present invention and discloses the fastening structure of the disposable diaper which dispenses with the front target tape for fastening the fastening piece on the surface of the belly side of the disposable diaper.

In the disposable diaper shown in FIG. 15, an absorbent body 43 comprising a floccular pulp, for example, has a certain rigidity and a rectangle or preferably an hourglass shape, as shown in FIG. 15, and is interposed between a liquid-permeable sheet 41 comprising a non-woven cloth or the like and a non-liquid permeable sheet which substantially does not allow the liquid to permeate therethrough, for example, a non-liquid permeable sheet 42 comprising polyethylene or the like which does not completely allow the liquid to permeate therethrough. This absorbent body 43 can be covered with upper and lower tissue papers for absorption and comprises an absorbent component.

The non-liquid permeable sheet 42 is a rectangle with a wider width than that of the absorbent component, and the external sheet 410, which comprises an hourglass-shaped non-woven cloth or the like, is provided outside the non-liquid permeable sheet.

The liquid-permeable sheet 41 is of a rectangle with wider width than that of the absorbent component, and is extended a little outwardly from the edge side of the absorbent component. The sheet 41 and the sheet 42 are bonded with the hot-melt adhesive or the like.

On both side portions of the disposable diaper, a leg periphery rising cuff C which protrudes toward the use side is formed, and the rising cuffs C form rising cuffs 44. The rising cuffs 44 include a breathable non-woven cloth or the like that is substantially continuous in a width direction and an elastic member, such as a leg peripheral elastic member 45 comprising a one piece fiber rubber or a plurality of fiber rubbers as shown in FIG. 15. A fastening piece 47 is a hook and loop fastener.

Further, the rising cuffs C are doubly formed by folding the internal surface side of the rising cuffs 44 in short-stages inwardly and each rising cuffs C envelopes each of the leg peripheral elastic members 45 therein, which are bonded with the hot-melt adhesive or the like.

The internal surface of the double-rising sheet 44 has a bonding start point at a position which is spaced out from the side edge of the liquid-permeable sheet 41, and the outward portion in the width direction is bonded with the hot-melt adhesive or the like from this bonding starting point to the extended edge of the non-liquid permeable sheet 42.

For the external surface of the double-rising sheet, the lower surface is bonded to the external sheet 410 with the hot-melt adhesive or the like.

As a result, the bonding starting point to the non-liquid permeable sheet 42 of the internal surface of the double-rising sheet 44 forms the rising start end of the rising cuff C. In the leg periphery portion, the inside of this rising end is the free portion which is not fixed at the body of the product and is divided in function and category into a rising portion which runs toward the central portion of the product and a plane usable portion which returns halfway and inverses toward the outside.

On the other hand, although not shown, in the forward and backward in the longitudinal direction, with the hot-melt adhesive or the like, the portion corresponding to the rising portion (the extended portion of the rising portion) is fixed in place at the product with the same running toward the central portion of the product, concretely the rising portion is fixed in place on the external surfaces of the liquid-permeable sheet 41 and the non-liquid permeable sheet 42, the portion corresponding to the plane usable portion (the extended portion of the plane usable portion) is fixed in place on the portion corresponding to the rising portion with the same returned and inversed.

In addition, although the basic form of the elastic members 45 is such that at least one of them is placed on the plane usable portion, it is preferred that particularly, the elastic member 45 is placed in the tip end of the plane usable portion, further it is preferred that the rising portion also has the elastic member 45.

The optimum embodiment is such that an elastic member is in the vicinity of the rising end, the vicinity of returning and the tip end of the plane usable portion. It is further preferable that the tip end of the plane usable portion has a plurality of elastic members as illustrated. The rising portion can be further provided with the elastic members 45, 45 to increase the rising force. In the embodiment as illustrated, there is the total of 6 pcs.

Figure 16:
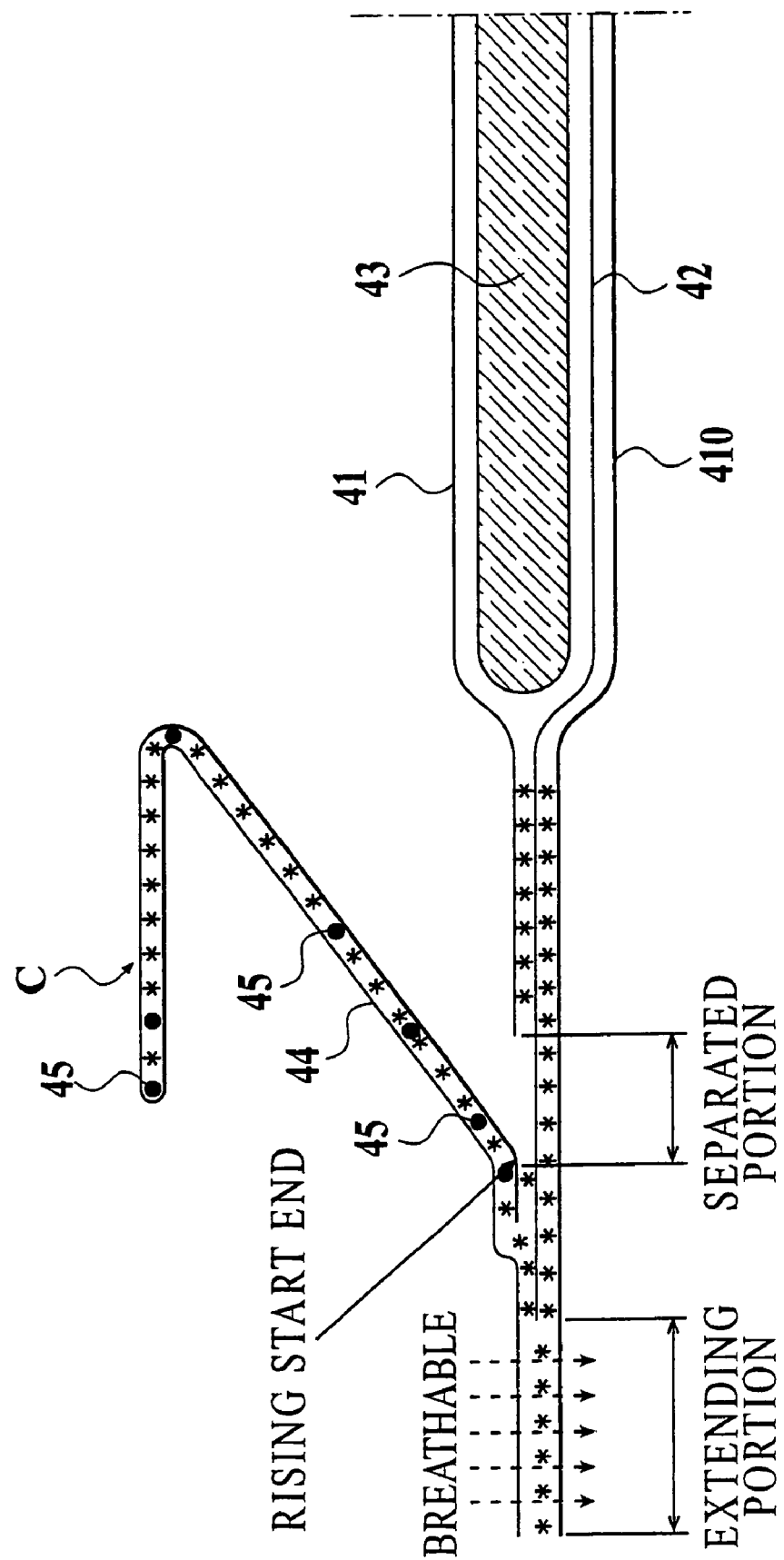
FIG. 16 is an arrow cross-section along a line of XVI-XVI in FIG. 15.

When the disposable diaper is put on, since the disposable diaper is put on a human body in a concave shape and the elastic members 45, 45 contact, as shown in FIG. 16 the rising cuffs B rise due to the contractile force of the elastic members 45, 45 in the leg periphery portion.

The space surrounded by the rising portion forms the containment space for urine or soft excrement. When a user urinates in this space, the urine is absorbed in the absorbent body 43 through the liquid-permeable sheet 41, and the over-flow of the solid in the soft excrement can be prevented since the rising portions of the rising cuffs C function as a barrier. When the urine overflows the rising distal side edge of the rising portion and leaks laterally, the lateral leakage can be prevented by the stop function of the plane usable portion.

In the embodiment, it is desirable that the rising sheet 44 which forms each rising cuff is not liquid-permeable, but is substantially non-liquid permeable (liquid-half permeable). In addition, silicon treatment may be performed on a liquid-permeable sheet (for example, a non-woven cloth) which forms the rising sheet to allow the sheet to have repellency of liquid. It is preferred that each of the rising sheet 44 and the external sheet 410 has the breathability, each of the rising sheet 44 and the external sheet 410 is a sheet with water resistance of 100 mmH$_2$O or more and is particularly made of a non-woven cloth. By this sheet, the side portion of the product in the width direction shows the breathability, thereby allowing to prevent the stuffiness of a wearer.

Particularly, by the product made of a non-woven cloth, when wearing the product, a sound is scarcely made, and the disposable diaper that feels like a cloth can be obtained. The material fiber of a non-woven cloth comprising the external sheet 410, the liquid-permeable sheet 41 and the rising sheet 44 can be made of regenerated fibers such as rayon, cupramonium rayon or the like and natural fibers such as cotton or the like as well as synthetic fibers of olefins series such as polyethylene, polypropylene or the like, polyester series, amide series or the like, and a non-woven cloth obtained by the suitable treatment methods such as a span bond method, a thermal bond method, a melt-blow method, a needle punch method or the like can be used.

In the embodiment according to the present invention, in a separated portion, since both the non-liquid permeable sheet 42 and the external sheet 410 are overlapped, the sheet is not broken in the developing and rising operation of the rising cuffs C.

<Fastening of Fastening Piece to Front Side of the Disposable Diaper>

In the present invention, a hook and loop fastener is used as a fastening piece 47 so that it can be mechanically fastened to the external sheet 410 comprising a non-woven cloth. Therefore, a so-called target tape may be also omitted, and the fastening position by fastening piece 47 can be freely selected.

Figure 19:
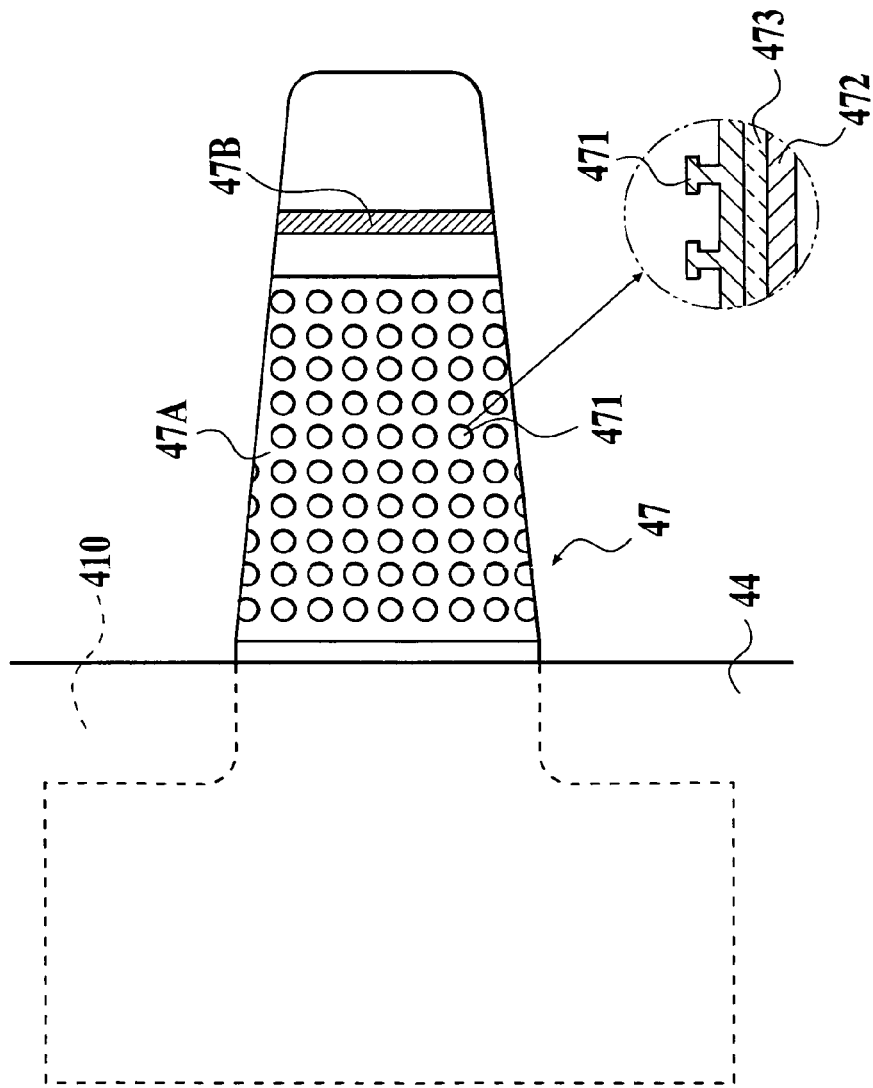
FIG. 19 is an explanatory view of a fastening piece.

For the fastening piece 47, the base of the fastening base material 472 such as plastic, poly laminate non-woven cloth and a paper as also shown in FIG. 19 is bonded to the external sheet 410, for example, by an adhesive, and the hook component 47A is provided at the tip side. The hook component 47A is bonded to the fastening base material 472 with the adhesive 473. The hook component 47A has a number of engagement pieces 471 on the external side thereof. As the shape of the engagement piece 471, there are provided L-shaped, J-shaped, mushroom-shaped, T-shaped or the like. The T-shaped one can be preferably used although any of the shapes may be used. A temporarily fastened bonded portion 47B is provided on the tip side from the hook component 47A. At the end of assembling the product, it is designed to prevent peeling-off of the tip side of the fastening piece 47 by allowing the temporarily fastened bonded portion 47B to be bonded to the rising sheet 44. When it is used, peeling-off is performed against the adhesion, the tip side of the fastening piece is brought into the front side. The tip side from the temporarily fastened bonded portion 47B forms a pick-up tab portion by allowing the fastening base material 472 to be exposed.

Figure 17:
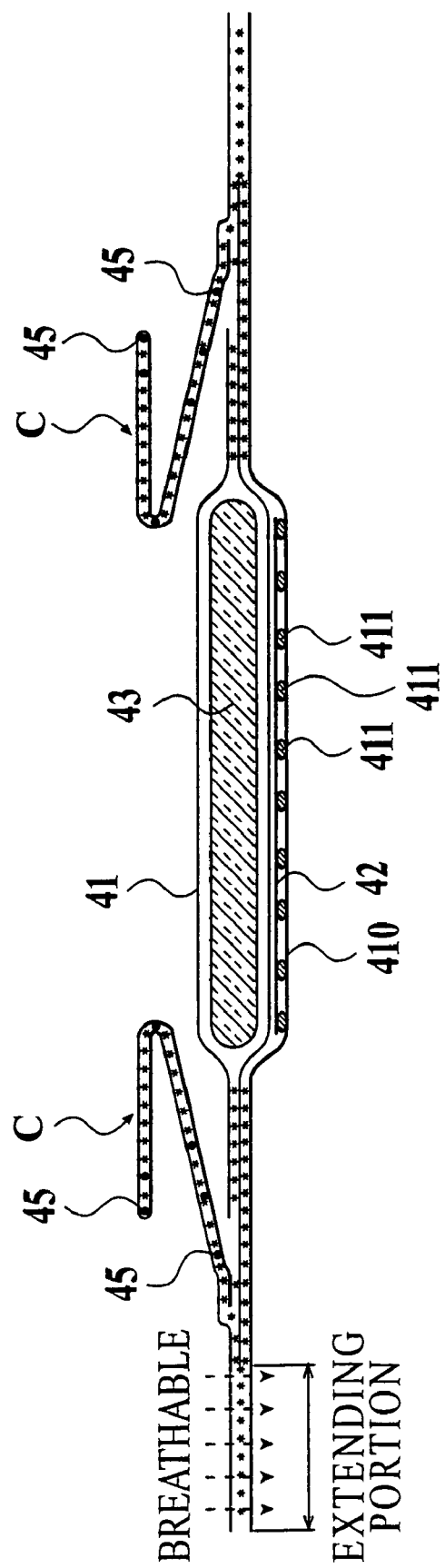
FIG. 17 is an arrow cross-section along a line of XVII-XVII in FIG. 15.
Figure 18:
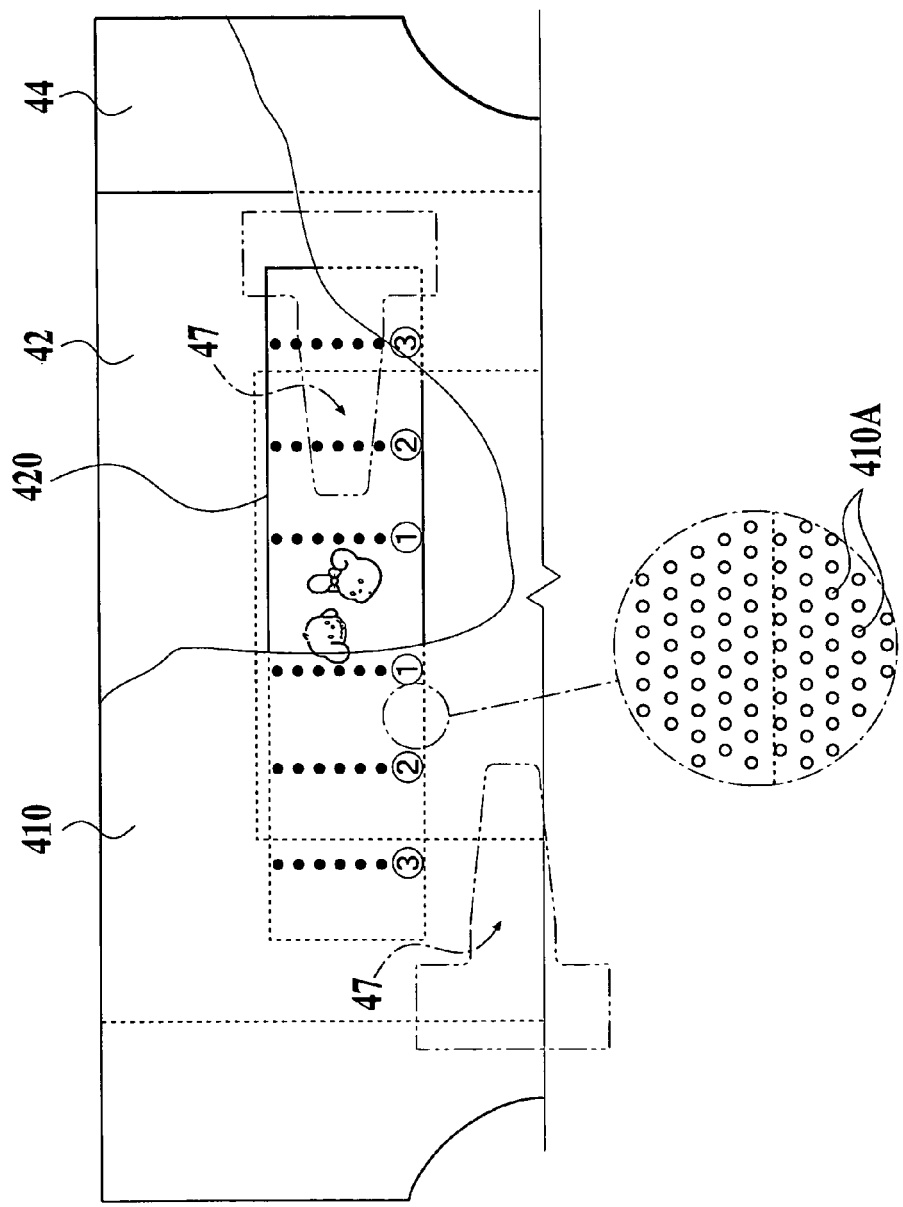
FIG. 18 is a front view in the front side of the product.

Referring particularly to FIG. 15, FIG. 17 and FIG. 18, on the opening portion of the front side, the target printed portion 420 is formed inside the external sheet 410, the target printing as the guidepost of a position for fastening the hook component 47A of the fastening piece 47 is performed, and it is arranged to be visually observed from the outside. In the embodiment as shown in the figure, the target printed portion 420 is performed on the non-liquid permeable sheet 42 comprising a polyethylene sheet which does not completely permeate the liquid, and the target printing is performed on the use side of the non-liquid permeable sheet 42. The target printing may be formed on the back side of the non-liquid permeable sheet 42. The target printed portion may be of the longitudinal length of 10-400 mm and of the body peripheral length of 50-500 mm. The target printing can be performed in photogravure or flexography. For the printing ink, a water-soluble ink is preferably used.

In at least the portion corresponding to the target printing, embossing of 7% per unit area is performed, for example, in a staggered pattern to the non-liquid permeable sheet 42 from the external surface of the external surface sheet 410 on the entire surface in the embodiment. The external sheet 410 and the non-liquid permeable sheet 42 are bonded on this embossed portion at a temperature of 160° C. or less with heat bonding. This heat bonded emboss portion 410A is, shown in FIG. 18. It is preferable that gigging is performed on the entire back surface of the external sheet 410 or at least on the portion thereof corresponding to the target printing.

On the other hand, the external sheet 410 and the non-liquid permeable sheet 42 are not entirely bonded with a hot-melt adhesive. Adhered (Adhering) areas 411, 411, by the hot-melt adhesive are spaced out, so that the external sheet 410 and the non-liquid permeable sheet 42 are bonded, for example, in a state of being spaced out in a stripe-shape.

Although a form of the target printed portion 420 may be voluntarily selected, it is desirable that the position in a width direction can be judged by the symbols of (1) to (3), color-coding by zone, the change of a pattern or the like. In addition, it is desirable that the entire target printed portion 420 is colored which can be distinguished from the color of the ambient. It is desirable that the thickness of printing is 10 to 50 μm.

It is preferable that the non-liquid permeable external sheet 410 comprises a fiber material of single fiber or long fiber, and the denier number thereof is 2.5 d or less.

It is preferable that the shear force of the surface of the relevant external sheet 410 with the hook component 47A is 50 g or more and the peel force thereof is 10 g or more. In addition, the sound when the mutually fastened surfaces of the fastening piece and the non-woven external sheet are peeled off is 12.0 sones or less.

The relevant shear force and peel force are each measured with the following "shear strength test method" and "peel strength test method".

Figure 12:
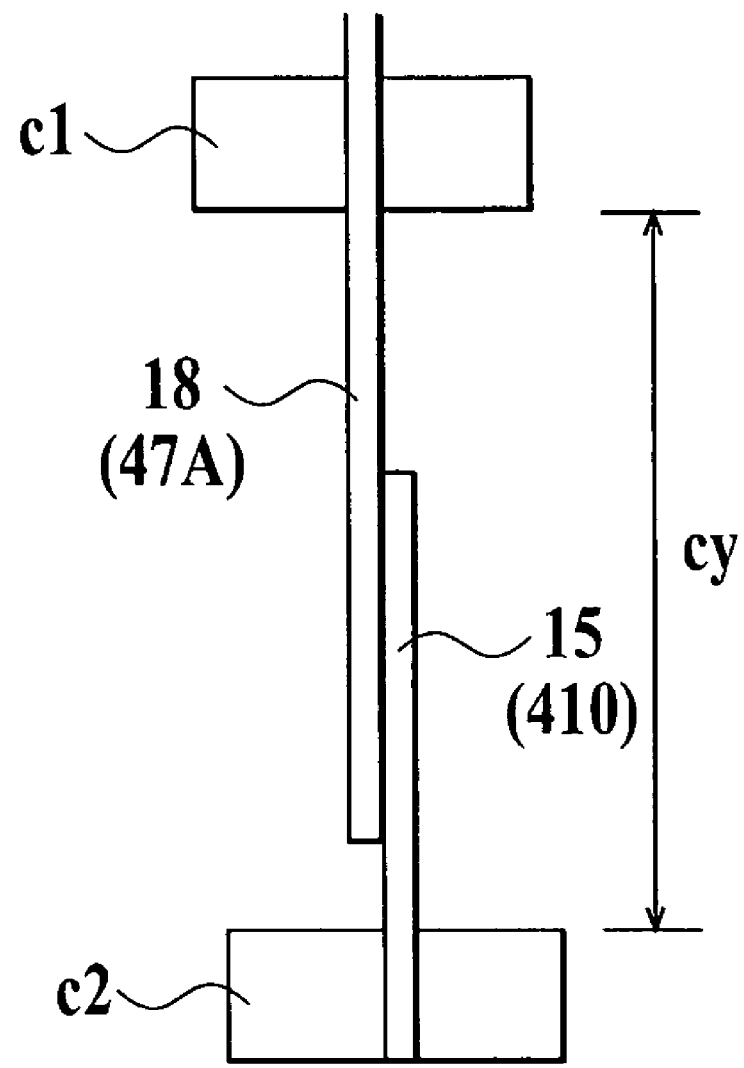
FIG. 12 is a view for explaining the manual of the shear force test method.

(A) Shear Strength Test Method (a) As shown in FIG. 12, an entire portion having a hook of the hook component 47A which is cut off out of the product is attached to the external sheet 410 which is cut into the size of 40 mm×100 mm from the disposable diaper. In this case, the direction of the external sheet 410 to the hook component 47A is the same as in the use of the product, that is, affixing is made so as to allow the longitudinal direction of the external sheet 410 in the product condition and the longitudinal direction of the hook component 47A in the product condition to be in parallel with each other.

(b) After that, the base end portion having no hook in the hook component 47A is chucked to the chuck c1 of the tensile testing machine and the unengaged portion in the external sheet 410 is chucked to the lower chuck, with a posture allowing the lateral direction in the product condition to be along the longitudinal direction, and controlling the distance cy between the upper and lower chucks c1, c2 to be 50 mm, pulling the object in the shearing direction at a tensile speed of 300 mm/min to perform measurement.

(c) The first peak obtained in the chart is read out which is determined to be the shear strength.

Figure 13A:
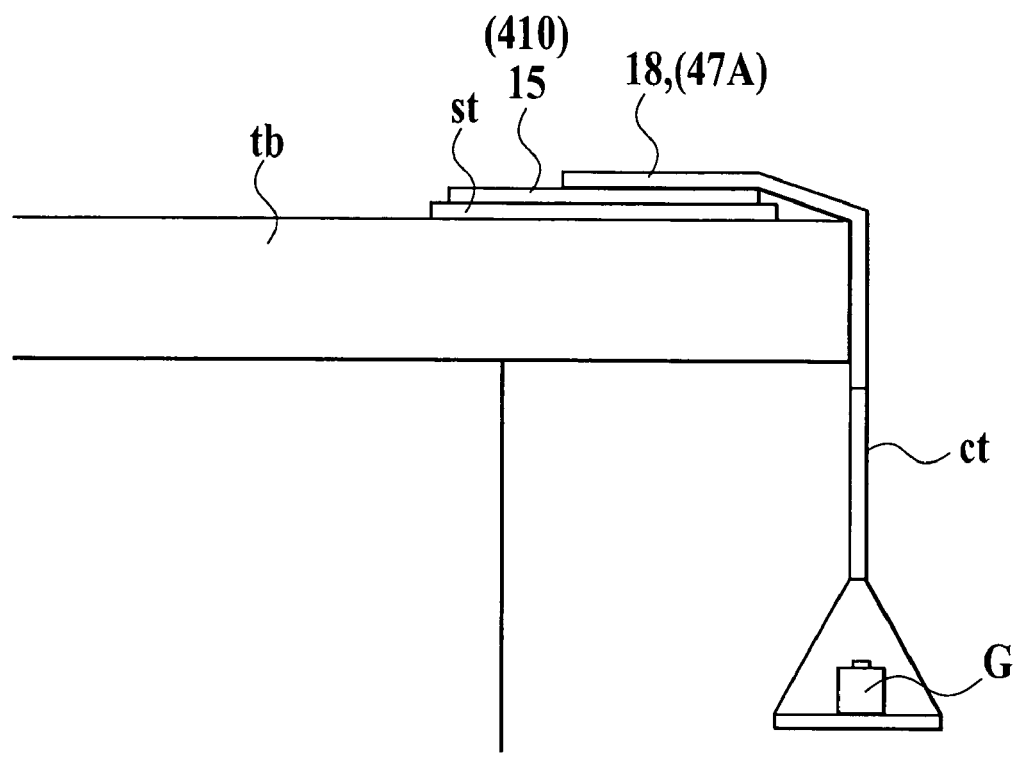
FIGS. 13A and 13B are views for explaining the manual of the peel strength test method.
Figure 13B:
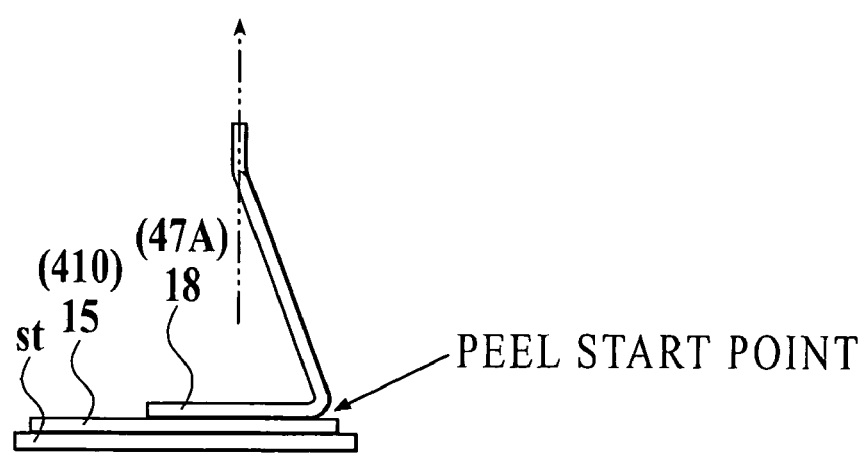

(B) Peel Strength Test Method (a) As shown in FIGS. 13A and 13B, the external sheet 410 is cut into the size of 40 mm×100 mm from the disposable diaper product. The back side of the external sheet 410 is attached with a double-sided adhesive tape to a stainless plate st with the side having the loops to be a front side. The end which is not fixed is fixed in place at the stainless plate st with a craft tape from the front surface side.

(b) Next, the entire portion having a hook of the hook component 47A that is cut off out of the product is attached to the front surface of the attached external sheet 410. In this case, the direction of the hook component 47A to the external sheet 410 is the same direction as in the use of the product, that is, affixing is made so as to allow the longitudinal direction of the external sheet 410 in the product condition and the longitudinal direction of the hook component 47A in the product condition to be in parallel with each other. After that, a roller with weight of 2 kg is shuttled back and forth once in the aforementioned longitudinal direction to engage the hook component 47A with the external sheet 410.

(c) Next, these stainless plate st, 410, 47A are fixed in place at the edge of the table tb or the like, the base end portion side having no hook on the hook component 47A is bent from edge of the table tb and is hung up, one end of the craft tape ct is attached to the hung portion, the weight G of 1 kg is mounted on the other end of the craft tape ct and a load is applied for two seconds.

(d) Next, the load is removed, and the hook receiving component which is engaged with the hook component is brought into the tensile testing machine which is not shown together with the stainless plate, and measurement is performed at a peel-off angle of 90° and at a tensile speed of 300 mm/min. This condition is shown in FIG. 13B.

(e) The maximum value and the minimum value are removed from the obtained chart, each three points of the maximum peaks and the minimum peaks (total: 6 points) are read out from the remaining peaks, and the average value is found which is determined to be a shear force.

On the other hand, the loudness of the sound (sone) in the present invention is the value which is found by assigning a value (phone) measured with a general noise meter when a peel-off is performed into the aforementioned equation (1).

In the aforementioned embodiment, the non-liquid permeable sheet 42 is formed by a polyethylene sheet and does not completely permeate the liquid and is of non-air permeable. However, as a non-liquid permeable sheet which does not substantially permeate the liquid, the breathability can be given in an embodiment in which a number of fine needle holes are formed in a non-liquid permeable sheet comprising a single polyethylene sheet or a poly laminate non-woven cloth internal surface side of which comprises a polyethylene sheet or the like and an external surface side of which comprises a non-woven cloth, or by forming the same with a high-density non-woven cloth.

Further, it is desirable that the one to which the moisture permeability is given is used. The air permeability between the skin side of the non-liquid permeable sheet which does not substantially permeate the liquid and the surface of the external sheet 410 is 5 cc/10 min or less.

As is clear from the foregoing, the disposable diaper in this embodiment can facilitate the tape fastening work while dispensing with a front target tape, eliminating troublesomeness when the fastening piece is fastened, improving a feel of wearing, improving productivity and reducing production cost.

EFFECT IN INDUSTRY

As mentioned above, the disposable diaper according to the present invention can facilitate a tape fastening work and is quite preferable for both infants and adults.

What is claimed is:

1. A disposable diaper comprising:
a hook and loop fastener which includes: (i) a plurality of hook components, which are fixed in place on both lateral sides of a rear side of the disposable diaper, and (ii) a hook receiving component that is fixed in place at a belly side of the disposable diaper, said hook components being engageable with the hook receiving component to form a fixing member for putting the disposable diaper on a user;
wherein the hook receiving component comprises:
a base material section having a printed target, which has a color-coded design, and which is visible from a front surface side of the hook receiving component so as to show a plurality of different fastening positions along a periphery of a body of the user; and
a plurality of loops which are disposed regularly and fixed in place on a surface of the base material section,
wherein each of the loops is formed of a non-crimp treated continuous filament yarn that is one of straight and slowly curved, a density of the loops is 10 to 50 loops/cm$^2$, a length of the loops is not more than 3 mm, each of the loops is inclined at a predetermined inclination with respect to the base material section and is not perpendicular to the base material section, and at least 80% of the loops are observed as being protruded toward the same lateral direction when the hook receiving component is viewed from a top,
wherein the loops are fixed to the base material section by a polyurethane series adhesive, and
wherein a thickness of each of the loops is 200 μm or less.

2. A disposable diaper comprising:
a hook and loop fastener which includes: (i) a plurality of hook components, which are fixed in place on both lateral sides of a rear side of the disposable diaper, and (ii) a hook receiving component that is fixed in place at a belly side of the disposable diaper, said hook components being engageable with the hook receiving component to form a fixing member for putting the disposable diaper on a user;
wherein the hook receiving component comprises:
a base material section having a printed target, which has a color-coded design, and which is visible from a front surface side of the hook receiving component so as to show a plurality of different fastening positions along a periphery of a body of the user;
a grid-like or net-like body comprising a grid-like or net-like filament yarn member; and a plurality of loops formed of a non-crimp treated continuous filament yarn which is one of straight and slowly curved, wherein the loops are continuous and are disposed regularly and fixed in place on a surface of the grid-like or net-like body, a density of the loops is 10 to 50 loops/cm$^2$, a length of the loops is not more than 3 mm, each of the loops is inclined at a predetermined inclination with respect to the base material section and is not perpendicular to the base material section, and at least 80% of the loops are observed as being protruded toward the same lateral direction when the hook receiving component is viewed from a top, wherein the loops are fixed to the base material section by a polyurethane series adhesive, and wherein a thickness of each of the loops is 200 μm or less.

3. The disposable diaper as claimed in claim 1 or claim 2, wherein the filament yarn of which the loops are formed is transparent or translucent, the target is printed by photogravure or flexography on the base material section on the same side as the loops are provided, and the hook receiving component has a light transmittance of not more than 60%.

* * * * *